(12) United States Patent
Sharpe et al.

(10) Patent No.: US 10,274,414 B2
(45) Date of Patent: Apr. 30, 2019

(54) PARTICLE PROCESSING SYSTEMS AND METHODS FOR NORMALIZATION/CALIBRATION OF SAME

(71) Applicant: CYTONOME/ST, LLC, Boston, MA (US)

(72) Inventors: Johnathan Charles Sharpe, Hamilton (NZ); Emanuel Tito Mendes Machado, Merrimack, NH (US); Rudolf Hulspas, Maynard, MA (US)

(73) Assignee: CYTONOME/ST, LLC, Bedford, MA (US)

( * ) Notice: Subject to any disclaimer, the term of this patent is extended or adjusted under 35 U.S.C. 154(b) by 562 days.

(21) Appl. No.: 14/281,353

(22) Filed: May 19, 2014

(65) Prior Publication Data
US 2014/0343869 A1    Nov. 20, 2014

Related U.S. Application Data

(63) Continuation of application No. 13/022,525, filed on Feb. 7, 2011, now Pat. No. 8,731,860.

(60) Provisional application No. 61/337,581, filed on Feb. 5, 2010.

(51) Int. Cl.
| | | |
|---|---|---|
| *G01N 15/14* | (2006.01) | |
| *G01N 15/10* | (2006.01) | |
| *G01N 21/53* | (2006.01) | |
| *G01N 21/64* | (2006.01) | |

(52) U.S. Cl.
CPC ..... *G01N 15/1484* (2013.01); *G01N 15/1012* (2013.01); *G01N 15/1429* (2013.01); *G01N 15/1459* (2013.01); *G01N 21/53* (2013.01); *G01N 21/64* (2013.01); *G01N 15/1056* (2013.01); *G01N 2015/1018* (2013.01); *G01N 2015/1075* (2013.01); *G01N 2015/1402* (2013.01); *G01N 2015/149* (2013.01)

(58) Field of Classification Search
None
See application file for complete search history.

(56) References Cited

U.S. PATENT DOCUMENTS

| | | | |
|---|---|---|---|
| 7,492,522 | B2 | 2/2009 | Gilbert et al. |
| 8,154,724 | B2 | 4/2012 | Mitchell et al. |
| 8,731,860 | B2 | 5/2014 | Charles et al. |
| 2005/0112541 | A1 | 5/2005 | Durack et al. |
| 2006/0244964 | A1 | 11/2006 | Cox et al. |
| 2008/0087068 | A1 | 4/2008 | Roth et al. |
| 2008/0108146 | A1 | 5/2008 | Jiang |
| 2008/0145286 | A1 | 6/2008 | Maltezos et al. |
| 2009/0109436 | A1 | 4/2009 | Shinoda |
| 2010/0220321 | A1 | 9/2010 | Kao et al. |
| 2011/0069311 | A1 | 3/2011 | Takeda |
| 2011/0217694 | A1* | 9/2011 | Buzatu ............. C12Q 1/06 435/5 |
| 2013/0080082 | A1 | 3/2013 | Howes et al. |
| 2013/0109050 | A1* | 5/2013 | Purvis, Jr. ......... G01N 15/1012 435/34 |

FOREIGN PATENT DOCUMENTS

| | | |
|---|---|---|
| WO | 2004088283 A2 | 10/2004 |
| WO | 2009146036 A2 | 12/2009 |
| WO | 2011/097032 A1 | 8/2011 |

OTHER PUBLICATIONS

Invitation to Pay Additional Fees and, Where Applicable, Protest Fees in PCT/US2011/023945, dated Jun. 6, 2011.
International Search Report and Written Opinion in PCT/US2011/023945, dated Jul. 29, 2011.
International Search Report for International Application No. PCT/US2011/023945 dated Jul. 29, 2011.
International Preliminary Report on Patentability and Written Opinion for International Application No. PCT/US2011/023945 dated Aug. 7, 2012.
International Search Report for International Application No. PCT/US2011/000211 dated Apr. 14, 2011.
International Preliminary Report on Patentability and Written Opinion for International Application No. PCT/US2011/000211 dated Aug. 7, 2012.
Communication pursuant to Article 94(3) EPC issued in European Patent Application No. 11707946.7, dated Nov. 13, 2014.
Exam Report dated Nov. 13, 2014 in related European Patent Application No. 11707946.7, 7 pages.
Exam Report dated Oct. 10, 2015 in related European Patent Application No. 11707946.7, 5 pages.

* cited by examiner

*Primary Examiner* — Michael L Borin
(74) *Attorney, Agent, or Firm* — McCarter & English, LLP; David R. Burns

(57) ABSTRACT

Systems, methods and non-transitory storage medium are disclosed herein for adjusting an output of a particle inspection system representative of a particle characteristic for a particle flowing in a flow-path of a particle processing system. More particularly, the output may be processed and a calibrated output of the particle characteristic generated. In other embodiments, one or more calibration particles are used. Thus, an output of a particle inspection system representative of a particle characteristic for one or more calibration particles flowing in a flow-path of a particle processing system may be compared relative to a standard and an action may be taken based on a result of the comparing the output to the standard.

15 Claims, 19 Drawing Sheets

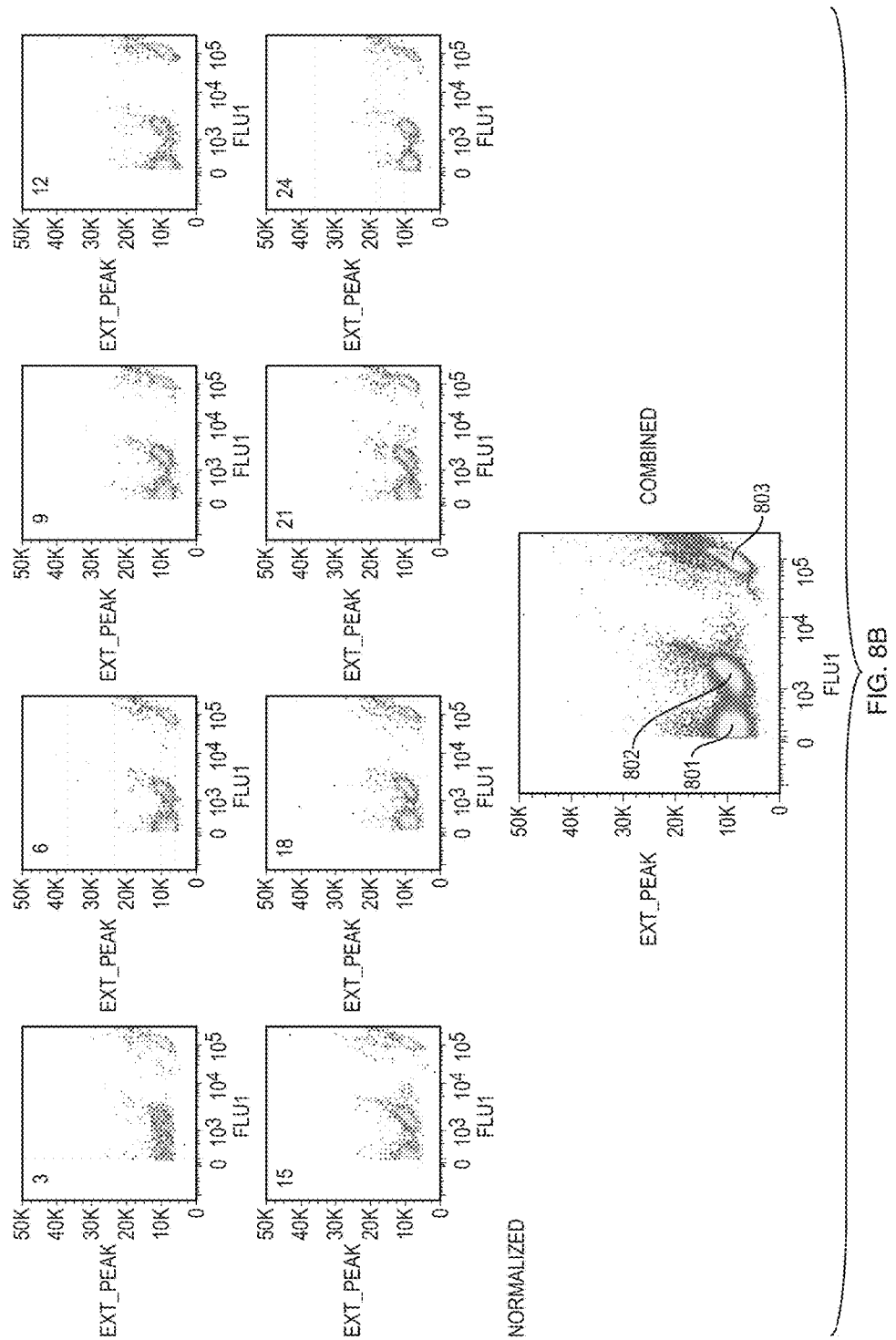

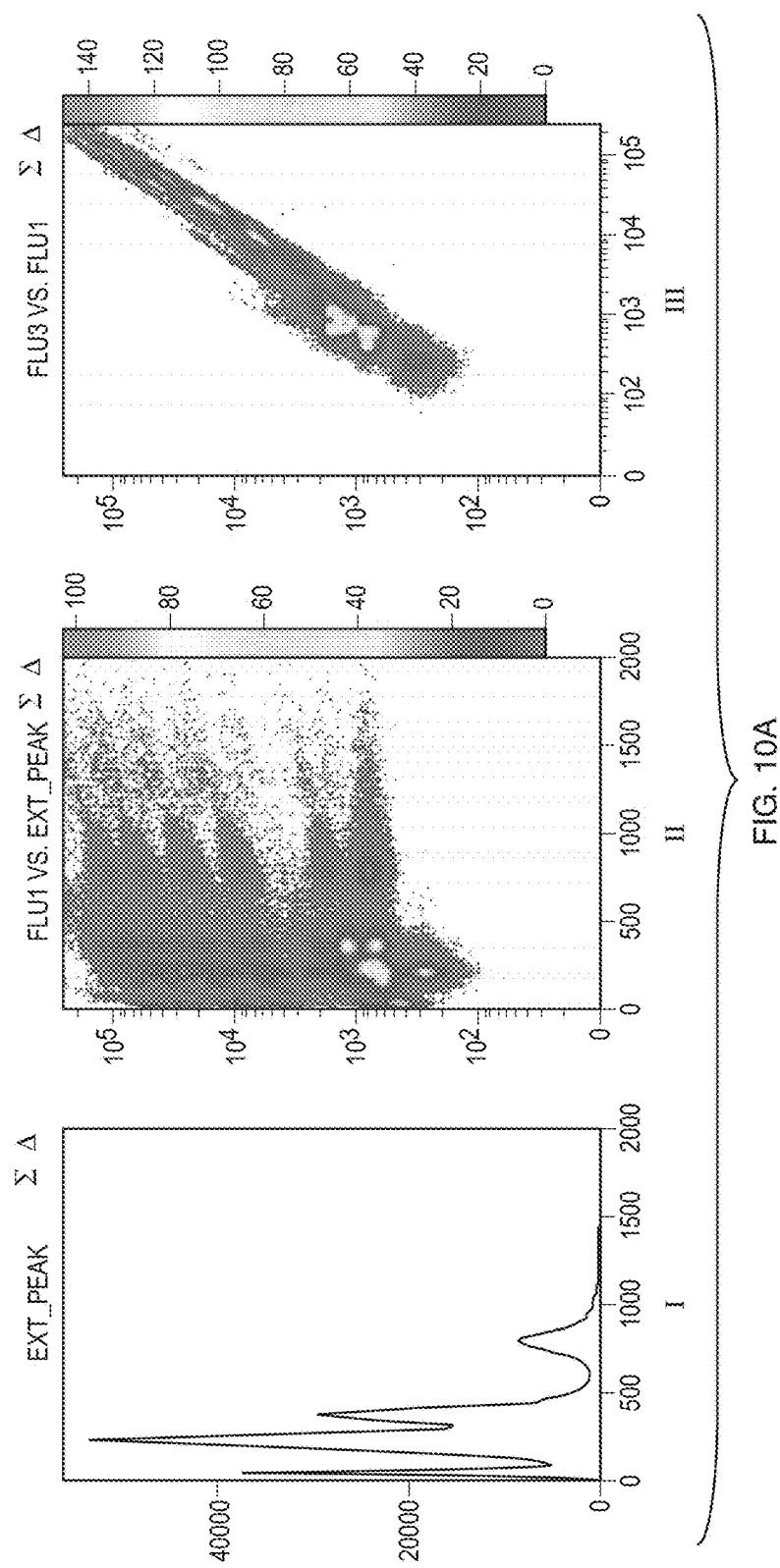

| | BLANK | URp2 | URp3 | URp4 | URp5 | URp6 |
|---|---|---|---|---|---|---|
| FLU1 | 210 | 1800 | | | 104400 | |
| FLU2 | 435 | 1700 | | | 110500 | |
| FLU3 | 522 | | 10888 | | 82674 | |
| FLU4 | 253 | | | 11851 | | 235928 |

| # BRB   |         |         |         |         |   |
|---------|---------|---------|---------|---------|---|
| 0       |         |         |         |         |   |
| # CH    | EXTPK   | EXTINT  |         |         |   |
| 3       | 2.1717  | 2.73113 |         |         |   |
| 7340    | 2.28554 | 0       | 0       | 0       | 0 |
| 7544    | 0       | 1.88199 | 0       | 0       | 0 |
| 7673    | 0       | 0       | 3.70907 | 0       | 0 |
| 7494    | 0       | 0       | 0       | 20.0729 | 0 |
| 7081    | 0       | 0       | 0       | 0       | 1 |
| # CH    | EXTPK   | EXTINT  |         |         |   |
| 6       | 2.1717  | 2.73113 |         |         |   |
| 7332    | 2.28554 | 0       | 0       | 0       | 0 |
| 7344    | 0       | 1.88199 | 0       | 0       | 0 |
| 7345    | 0       | 0       | 3.70907 | 0       | 0 |
| 7725    | 0       | 0       | 0       | 20.0729 | 0 |
| 7028    | 0       | 0       | 0       | 0       | 1 |
| # BRB   |         |         |         |         |   |
| 1       |         |         |         |         |   |
| # CH    | EXTPK   | EXTINT  |         |         |   |
| 3       | 1.58614 | 2.16091 |         |         |   |
| 7302    | 4.98053 | 0       | 0       | 0       | 0 |
| 6945    | 0       | 4.47068 | 0       | 0       | 0 |
| 7403    | 0       | 0       | 7.96711 | 0       | 0 |
| 6945    | 0       | 0       | 0       | 38.303  | 0 |
| 7197    | 0       | 0       | 0       | 0       | 1 |
| # CH    | EXTPK   | EXTINT  |         |         |   |
| 6       | 1.75284 | 2.13611 |         |         |   |
| 7386    | 2.85041 | 0       | 0       | 0       | 0 |
| 7395    | 0       | 2.61287 | 0       | 0       | 0 |
| 7690    | 0       | 0       | 3.95174 | 0       | 0 |
| 7515    | 0       | 0       | 0       | 14.2947 | 0 |
| 7159    | 0       | 0       | 0       | 0       | 1 |

FROM FIG 18A

| # BRB | | | | | |
|---|---|---|---|---|---|
| 2 | | | | | |
| # CH | EXTPK | EXTINT | | | |
| 3 | 1.11519 | 1.61172 | | | |
| 7371 | 2.12321 | 0 | 0 | 0 | 0 |
| 7670 | 0 | 0.99850 | 0 | 0 | 0 |
| 8103 | 0 | 0 | 1.95993 | 0 | 0 |
| 7828 | 0 | 0 | 0 | 8.37653 | 0 |
| 7116 | 0 | 0 | 0 | 0 | 1 |
| # CH | EXTPK | EXTINT | | | |
| 6 | 0.506264 | | 0.726108 | | |
| 7560 | 1.64771 | 0 | 0 | 0 | 0 |
| 7808 | 0 | 1.2664 | 0 | 0 | 0 |
| 8170 | 0 | 0 | 2.48879 | 0 | 0 |
| 9504 | 0 | 0 | 0 | 8.0625 | 0 |
| 7100 | 0 | 0 | 0 | 0 | 1 |
| # BRB | | | | | |
| 3 | | | | | |
| # CH | EXTPK | EXTINT | | | |
| 3 | 1.62906 | 2.74855 | | | |
| 7525 | 2.72174 | 0 | 0 | 0 | 0 |
| 7590 | 0 | 1.78093 | 0 | 0 | 0 |
| 7963 | 0 | 0 | 3.40438 | 0 | 0 |
| 7606 | 0 | 0 | 0 | 18.1313 | 0 |
| 7083 | 0 | 0 | 0 | 0 | 1 |
| # CH | EXTPK | EXTINT | | | |
| 6 | 1.21881 | 1.58071 | | | |
| 7332 | 1.43445 | 0 | 0 | 0 | 0 |
| 7689 | 0 | 1.36877 | 0 | 0 | 0 |
| 7683 | 0 | 0 | 1.9845 | 0 | 0 |
| 7779 | 0 | 0 | 0 | 11.8306 | 0 |
| 7032 | 0 | 0 | 0 | 0 | 1 |

FIG. 18B

PARTICLE PROCESSING SYSTEMS AND METHODS FOR NORMALIZATION/CALIBRATION OF SAME

CROSS-REFERENCE TO RELATED APPLICATION

This application is a continuation of U.S. patent application Ser. No. 13/245,132, filed Sep. 26, 2011, which claims priority to priority to U.S. Provisional Application No. 61/337,581, filed on Feb. 5, 2010, the contents of each application is incorporated herein by reference in their entirety.

TECHNICAL FIELD

The present disclosure relates to particle processing, for example particle sorting. More particularly, the present disclosure relates to normalization/calibration of particle measurements used for particle processing.

BACKGROUND

In the fields of biotechnology, biology and medicine, there is a need for high throughput processing (for example, analysis and sorting) of particles. High throughput particle processing may be facilitated by utilizing multiple flow-paths in parallel. Furthermore, multiple particle processing systems, in the same or different physical locations, may be utilized to carry out the same or similar particle processing operations.

Conventionally, particle processing involves analyzing one or more particles within a flow-path and processing (for example, sorting) the particle(s) based on such analysis. As described in Application No. U.S. Application No. 61/429,339, particle processing may also involve analyzing processed particles(s) to evaluate, for example, processing errors. Various particle measurements may be used to analyze (for example, characterize, group and/or differentiate between) particle(s) within, for example, flowing in or along, a flow-path. Accuracy, consistency and reliability of such particle measurements is paramount for effective particle processing. These and other needs are addressed by way of the present disclosure.

SUMMARY

Systems, methods and non-transitory computer readable storage medium are presented herein related to particle detection using a particle inspection system in a particle processing system.

In exemplary embodiments, a particle processing system is presented including a particle inspection system configured to detect a particle characteristic of a particle flowing in a flow path of the particle processing system; and a processor programmed to processes an output of the particle inspection system representative of the particle characteristic for the particle to generate a calibrated output of the particle characteristic. In some embodiments, the particle characteristic may be a multi-dimensional particle characteristic. In other embodiments, the output may be derived from processing data from one or more detectors in the particle inspection system. In some embodiments the processing the output standardizes measurement of the particle characteristic. In exemplary embodiments, the calibrated output may be standardized to conform to a reference scale of measurement for the particle characteristic. In some embodiments, the processing the output may provide a common basis for comparing the calibrated output relative to a second output representative of the particle characteristic obtained with a different particle inspection system. In other embodiments, the processing the output may provide a common basis for comparing the calibrated output relative to a second output representative of the particle characteristic obtained for a particle in a different region of the flow-path or in a different flow-path. In yet other embodiments, the processing the output may provide a common basis for relating the calibrated output relative to an output representative of a different particle characteristic. In some embodiments, the processing the output may include calibrating the output based on a velocity of the particle. For example, the processing the output may include calibrating the output with respect to an average particle velocity (such as adjusting the output by a factor of a velocity of the particle over an average particle velocity) or calibrating the output with respect to a standard particle velocity (such as adjusting the output by a factor of a velocity of the particle over a standard particle velocity). In exemplary embodiments, the processing the output may include applying one or more correction factors which may be applied, for example, using a matrix mechanism. In some embodiments, processing the output may include adjusting a baseline for the output. In exemplary embodiments, adjusting the baseline may includes mitigating baseline variability, for example, by dividing the baseline by an average baseline.

In exemplary embodiments, a particle processing system is presented including a particle inspection system configured to detect a characteristic for one or more calibration particles flowing in a flow-path of the particle processing system; and a processor programmed to compare an output representative of the particle characteristic for the one or more calibration particles relative to a standard and take an action based on a result of the comparing the output to the standard. In some embodiments, the processor may be further programmed to determine, based on the comparing of the output relative to the standard, one or more correction factors for calibrating data obtained by the particle inspection system, for example using a fitting function or multidimensional envelope to relate the one the output to the standard. In other embodiments, the processor may be further programmed to adjust, based on the comparing of the output relative to the standard, one or more operating parameters of the particle inspection system. In yet other embodiments, the processor may be further programmed to determine, based on the comparing of the output relative to the standard, one or more correction factors for tailoring an algorithm for processing or analyzing data obtained by the particle inspection system. In some embodiments, the comparing the output relative to the standard may include identifying one or more clusters of measurement values for the particle characteristic, each cluster representative of a population of the calibration particles. The one or more clusters may, for example, be determined by using a cluster finding algorithm and/or based on a pattern of clusters.

In exemplary embodiments, a particle processing system is presented including a particle inspection system configured to detect a characteristic for a particle flowing in a flow-path of the particle processing system; and a processor programmed to adjust a first output of the particle inspection system representative of the particle characteristic for the particle to provide a common basis for comparing the adjusted first output relative to a second output. In some embodiments, the second output may be representative of the same particle characteristic. In other embodiments the second output may be representative of a different particle characteristic. In some embodiments, the second output may be representative of a particle characteristic for a different particle. In some embodiments, the second output may be representative of a particle characteristic for a particle in a different detection region in the flow-path. In other embodiments, the second output may be representative of a particle characteristic for a particle in a different flow-path in the particle processing system. In yet other embodiments, the second output may be representative of a particle characteristic for a particle in a different particle processing system. In some embodiments, the second output may be detected with a different particle inspection system. In some embodiments, the processor may be further configured to superimpose the first and second outputs. In exemplary embodiments, the superimposed first and second outputs may be viewed in combination on a display.

In exemplary embodiments, a particle processing system is presented including a particle inspection system configured to detect a characteristic for a particle flowing in a flow-path of the particle processing system; and a processor programmed to superimpose a first output of the particle inspection system representative of the particle characteristic for the particle relative to a second output. In some embodiments, the second output may be representative of the same particle characteristic. In other embodiments the second output may be representative of a different particle characteristic. In some embodiments, the second output may be representative of a particle characteristic for a different particle. In some embodiments, the second output may be representative of a particle characteristic for a particle in a different detection region in the flow-path. In other embodiments, the second output may be representative of a particle characteristic for a particle in a different flow-path in the particle processing system. In yet other embodiments, the second output may be representative of a particle characteristic for a particle in a different particle processing system. In some embodiments, the second output may be detected with a different particle inspection system. In exemplary embodiments, the superimposing the first and second outputs includes adjusting the first output to provide a common basis for comparing the adjusted first output relative to the second output. In exemplary embodiments, the superimposed first and second outputs may be viewed in combination on a display.

In exemplary embodiments, a particle monitoring system is presented including a receiver configured to receive data from a plurality of particle inspections systems concerning a population of particles, and a processor programmed to processes the received data to account for measurement or processing variability amongst the plurality of particle inspection systems. In some embodiments, the plurality of particle inspection systems may be co-located on a microfluidic chip or associated with a same particle processing system. In other embodiments, the plurality of particle inspection systems may be located on different microfluidic chips or associated with different particle processing systems. In some embodiments, the plurality of particle inspection systems may be located at geographically distinct locations.

In exemplary embodiments, a particle processing system is presented including a particle inspection system configured to detect a characteristic for a calibration particle flowing in a flow-path of the particle processing system; and a processor programmed to determine a measurement value for the characteristic for the calibration particle, compare the measurement value to a standard; and take an action based on a result of the comparing the measurement value to the standard. In some embodiments, the processor may be further programmed to determine, based on the comparing of the measurement value relative to the standard, one or more correction factors for calibrating data obtained by the particle inspection system, for example, wherein the one or more correction factors are determined by using a fitting function to relate the measurement value to the standard. In other embodiments, the processor may be further programmed to adjust, based on the comparing of the measurement value relative to the standard, one or more operating parameters of the particle inspection system. In yet other embodiments, the processor may be programmed to determine, based on the comparing of the measurement value relative to the standard, one or more correction factors for tailoring an algorithm for processing or analyzing data obtained by the particle inspection system.

In exemplary embodiments, a method is presented including steps of measuring with a particle inspection system a particle characteristic for a particle flowing in a flow-path of the particle processing system; and calibrating an output from the particle inspection system representative of the particle characteristic for the particle to generate a calibrated output representative the particle characteristic. In some embodiments, the calibrated output may be used to control processing of the particle by the particle processing system. In other embodiments, the calibrated output may be used to evaluate a processing of the particle by the particle processing system. In some embodiments, the calibrating the output may standardize measurement of the particle characteristic. For example, the calibrated output may be standardized to conform to a reference scale of measurement for the particle characteristic. In some embodiments, the calibrating the output may provide a common basis for comparing the calibrated output relative to a second output representative of the particle characteristic obtained with a different particle inspection system. In other embodiments, the calibrating the output may provide a common basis for comparing the calibrated output relative to a second output representative of the particle characteristic obtained for a particle in a different region of the flow-path or in a different flow-path. In yet other embodiments, the calibrating the output may provide a common basis for relating the calibrated output relative to an output representative of a different particle characteristic. In some embodiments, the calibrating the output may include calibrating the output based on a velocity of the particle. In other embodiments, the calibrating the output may include adjusting a baseline for the output.

In exemplary embodiments, a method is presented including steps of detecting with a particle inspection system a characteristic for one or more calibration particles flowing in a flow-path of the particle processing system; determining an output representative of the characteristic for the one or more calibration particles; comparing the output relative to a standard; and taking an action based on a result of the comparing the output relative to the standard. In some embodiments, the action may include calculating, based on the comparing of the output relative to the standard, one or more correction factors for calibrating data obtained by the particle inspection system, for example, wherein the one or more correction factors may be determined by using a fitting function or a multi-dimensional envelope to relate the output to the standard. In other embodiments, the action may include adjusting, based on the comparing of the output relative to the standard, one or more operating parameters of the particle inspection system. In yet other embodiments, the action may include calculating, based on the comparing of the output relative to the standard, one or more correction factors for tailoring an algorithm for processing or analyzing data obtained by the particle inspection system. In some embodiments, the calibration particles may be selected to include identifiable populations with respect to the particle characteristic. In exemplary embodiments, the standard may include reference values for the particle characteristic for one or more calibration particles or for one or more populations of calibration particles. In some embodiments, the standard may be selected to set a dynamic range or resolution for the particle characteristic, for example, to optimize a dynamic range or resolution for the particle characteristic with respect to a target population of particles. In exemplary embodiments, the comparing the output relative to the standard includes identifying one or more clusters of measurement values for the particle characteristic, each cluster representative of a population of the calibration particles.

In exemplary embodiments, a method is presented including steps of detecting, with a particle inspection system a first output representative of a particle characteristic for a particle flowing in a flow path of a particle processing system; and adjusting the first output of a particle inspection system to provide a common basis for comparing the adjusted first output relative to a second output. In some embodiments, the second output may be representative of the same particle characteristic. In other embodiments the second output may be representative of a different particle characteristic. In some embodiments, the second output may be representative of a particle characteristic for a different particle. In some embodiments, the second output may be representative of a particle characteristic for a particle in a different detection region in the flow-path. In other embodiments, the second output may be representative of a particle characteristic for a particle in a different flow-path in the particle processing system. In yet other embodiments, the second output may be representative of a particle characteristic for a particle in a different particle processing system. In some embodiments, the second output may be detected with a different particle inspection system. In exemplary embodiments, the processor may be further configured to superimpose the first and second outputs. In some embodiments, the superimposed first and second outputs may be viewed in combination on a display. In exemplary embodiments, the superimposed first and second outputs may be viewed in combination on a display.

In exemplary embodiments, a method is presented including steps of detecting, with a particle inspection system a first output representative of a particle characteristic for a particle flowing in a flow path of a particle processing system; and superimposing the first output relative to a second output. In some embodiments, the second output may be representative of the same particle characteristic. In other embodiments the second output may be representative of a different particle characteristic. In some embodiments, the second output may be representative of a particle characteristic for a different particle. In some embodiments, the second output may be representative of a particle characteristic for a particle in a different detection region in the flow-path. In other embodiments, the second output may be representative of a particle characteristic for a particle in a different flow-path in the particle processing system. In yet other embodiments, the second output may be representative of a particle characteristic for a particle in a different particle processing system. In some embodiments, the second output may be detected with a different particle inspection system. In exemplary embodiments, the superimposing the first and second outputs includes adjusting the first output to provide a common basis for comparing the adjusted first output relative to the second output. In some embodiments, the superimposed first and second outputs may be viewed in combination on a display.

In exemplary embodiments, a method is presented including steps of detecting with a particle inspection system a characteristic for a calibration particle flowing in a flow-path of the particle processing system; determining a measurement value for the characteristic for the calibration particle; comparing the measurement value to a standard; and taking an action based on a result of the comparing the measurement value to the standard. In some embodiments, the action may include determining, based on the comparing of the measurement value relative to the standard, one or more correction factors for calibrating data obtained by the particle inspection system, for example, wherein the one or more correction factors are determined by using a fitting function to relate the measurement value to the standard. In other embodiments, the action may include adjusting, based on the comparing of the measurement value relative to the standard, one or more operating parameters of the particle inspection system. In yet other embodiments, the action may include determining, based on the comparing of the measurement value relative to the standard, one or more correction factors for tailoring an algorithm for processing or analyzing data obtained by the particle inspection system.

In exemplary embodiments, a non-transitory computer-readable storage medium is presented storing computer executable instructions for processing an output of a particle inspection system representative of a particle characteristic for a particle flowing in a flow-path of a particle processing system; and generating a calibrated output of the particle characteristic.

In other exemplary embodiments, a non-transitory computer-readable storage medium is presented storing computer executable instructions for comparing an output of a particle inspection system representative of a particle characteristic for one or more calibration particles flowing in a flow-path of a particle processing system relative to a standard; and taking an action based on a result of the comparing the output to the standard.

Additional features, functions and benefits of the disclosed systems, methods and medium will be apparent from the description which follows, particularly when read in conjunction with the appended figure.

BRIEF DESCRIPTION OF THE DRAWINGS

FIGS. 8A-8B depict light extinction versus fluorescence for a plurality of flow-channels individually and in combination before and after measurement adjustment, according to the present disclosure.

FIGS. 10A-10B depict bivariate plots of light extinction versus particle size, fluorescence versus light extinction, and fluorescence 3 versus fluorescence 1, for a combined plurality of flow-channels before and after measurement adjustment, according to the present disclosure.

FIGS. 18A-18B depict exemplary correction factors matrixes for a plurality of flow-channels, according to the present disclosure.

DESCRIPTION OF EXEMPLARY EMBODIMENT(S)

Figure 1:
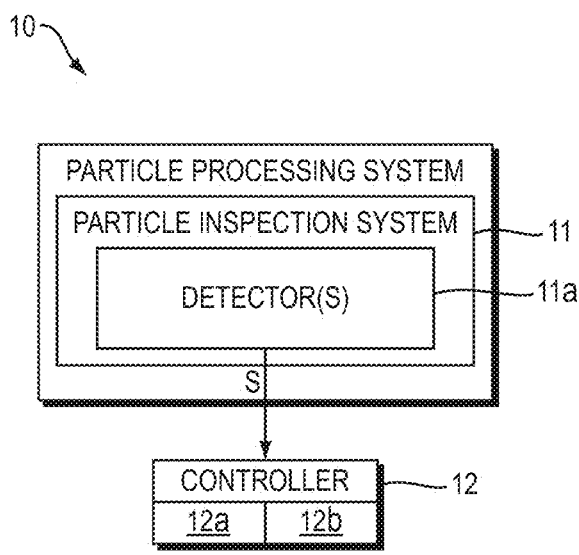
FIG. 1 depicts and exemplary particle processing system, according to the present disclosure.

Systems, methods and non-transitory storage medium are disclosed herein for adjusting for example, normalizing, calibrating and/or standardizing, an output, for example a measurement value, of a particle inspection system representative of a particle characteristic for a particle in a flow-path of a particle processing system. In some embodiments, the output may be adjusted to reduce/minimize instrument-related measurement variability, for example, for measurements by the particle inspection system or between particle inspection systems, or for measurement for different particles, different detection regions, different flow-paths, or different particle processing systems. In other embodiments, the output may be adjusted to reduce/minimize particle-velocity-related measurement variability, for example, for measurements by the particle inspection system or between particle inspection systems, or for measurement for different particles, different detection regions, different flow-paths, or different particle processing systems. In some embodiments, the output may be adjusted to reduce/minimize baseline variability (for example, due to low frequency power fluctuations in a light source in the case of optical detection, or the like), for example, for measurements by the particle inspection system or between particle inspection systems, or for measurement for different particles, different detection regions, different flow-paths, or different particle processing systems.

In some embodiments, the systems, methods and non-transitory storage medium disclosed herein may advantageously provide a common basis or baseline for comparing outputs representative of a same particle characteristic (for example, for different particles, different detection regions, different flow-paths, different particle inspection systems, and/or different particle processing systems) or for relating outputs representative of different particle characteristics. Thus, for example, a particle inspection system may be used to measure or detect a particle characteristic for a particle in a flow-path of a particle processing system. One or more corrective factors may then be applied to adjust, for example, normalize, calibrate, or standardize, an output from the particle inspection system representative of the particle characteristic.

In other embodiments, one or more calibration particles may be used to adjust measurement, detection and/or processing of a particle characteristic by a particle inspection system. For example, the particle inspection system may be used to measure or detect a particle characteristic for one or more calibration particles in a flow-path of a particle processing system. An output representative of the particle characteristic for the one or more calibration particles may then be compared relative to a standard, for example to determine a deviation therefrom and/or a correlation thereto. In some embodiments, measurement or detection of the particle characteristic, for example, for another particle, may be adjusted based on the comparison. For example, in some embodiments, measurement or detection of the particle characteristic may be adjusted by calculating and applying one or more correction factors. In other embodiments, measurement or detection of the particle characteristic may be adjusted by changing one or more operating parameters of the particle inspection system (for example light source power). In exemplary embodiments, measurement or detection of the particle characteristic may be adjusted to conform to the standard. In some embodiments, processing of the particle characteristic may be adjusted, based on the comparison. In exemplary embodiments, processing of the particle characteristic may include applying a processing algorithm as a function of the particle characteristic, for example, an algorithm for sorting particles as a function of the particle characteristic. Thus, in some embodiments processing of the particle characteristic may be adjusted by tailoring a standard processing algorithm for the particle inspection system.

Particle characteristics may include optical characteristics (fluorescence, scatter, absorbance, extinction, reflection, refraction, polarization, luminescence, chemiluminescence, phosphorescence, spectral/color), electrical characteristics, electromagnetic characteristics, magnetic characteristics, plasmonic characteristics, acoustic characteristics, chemical characteristics, biological characteristics, molecular characteristics, mechanical characteristics, or the like. In some embodiments, particle characteristics may be multi-dimensional for example, a multi-dimensional spectral/color measurement (RGB, CMYK, CIELAB, CIEXYZ, and the like). In exemplary embodiments, a measurement of a particle characteristic may be derived by processing/analyzing data from one or more detectors. Exemplary particle characteristics which may be derived by processing/analyzing data from one or more detectors may include particle size, geometry, volume, surface area, shape, elipticity, velocity, refractive index, granularity, porosity, conductivity, identity, type, phenotype, protein or molecular expression, biological pathway data, genetic content, live/dead state, function or the like.

Particle processing systems, according to the present disclosure, preferably utilize microfluidics and may comprise a closed-channel system for processing particles. Microfluidic particle processing technology takes advantages of a closed, sterile, and scalable approach to efficiently and/or quickly process large numbers of particles. To this end, a plurality of flow-channels may be combined, for example, on a single microfluidic chip substrate. Particle detection, analysis and/or processing (for example, sorting) functionalities may further interface with the chip or be included thereon.

The terms flow-path and flow-channel as used herein refer to a pathway formed in or through a medium that allows for movement of fluids, such as liquids and gases. Typical flow-channels in a microfluidic system have cross-sectional dimensions between about 1.0 µm and about 500 µm. In some embodiments, flow-channels have cross-sectional dimensions between about 25 µm and about 250 µm. In further embodiments, flow-channels have cross-sectional dimensions between about 50 µm and about 200 µm. One of ordinary skill in the art will be able to determine appropriate channel dimensions, for example, cross-sectional dimension, length, volume, or the like, of a flow-channel. A flow-channel can have any selected shape or arrangement, examples of which include but are not limited to a linear or non-linear configuration, a U-shaped configuration, a V-shaped configuration, a D-shaped configuration, a C-shaped configuration, a circular configuration, oval configuration, rectangular configuration or the like.

The term "particle" refers to a discrete unit of matter. For example, particles may include atoms, ions, molecules, cells, agglomerates, or the like. Particles may also refer to (macro) molecular species such as proteins, enzymes, polynucleotides, or the like. In some embodiments, particles may be between 1 nm and 10 mm in diameter. In other embodiments, particles may be between 100 nm and 200 µm in diameter. In yet other embodiments, particles may be between 1 µm and 15 µm in diameter. Particles may be naturally occurring or synthetic, or may combine natural and synthetic components within a single particle. Particles may refer to biological particles. For example, particles may include cells (for example, blood platelets, white blood cells, tumorous cells or embryonic cells, spermatozoa, to name a few), liposomes, proteoliposomes, yeast, bacteria, viruses, pollens algae, or the like. Particles may also refer to non-biological particles. For example, particles may include metals, minerals, polymeric substances, glasses, ceramics, composites, or the like. In exemplary embodiments, particles may include cells or beads with fluorochrome conjugated antibodies.

The term "detector," as used herein, refers to a device for detecting data. Detected data may, for example, be relevant to determining an output representative of a particle characteristic for a particle in a flow-path of a particle processing system.

The terms "upstream" and "downstream" are referenced relative to a directional flow of particles in a flow-path.

The term "standard" as used herein refers to a value, reference or reference point against which a measurement or detection may be evaluated.

With initial reference to FIG. 1, an exemplary particle processing system 10 is depicted. The particle processing system 10 may include one or more flow-paths for processing particles. The particle processing system 10 may further include or be operatively associated with a particle inspection system 11 including one or more detectors 11a for obtaining an output S representative of a particle characteristic for one or more particle in flow-path in the particle processing system 10. In some embodiments, the particle inspection system 11 may be a primary particle inspection system wherein the one or more detectors 11a are included in or operatively coupled directly or indirectly to the flow-path at or upstream from a particle processing region thereof. In other exemplary embodiments, the particle inspection system 11 may be a secondary particle inspection system, wherein the one or more detectors 11a are included in or operatively coupled directly or indirectly to the flow-path at or downstream from a particle processing region thereof. In some embodiments, such as where the particle inspection system 11 is a primary particle inspection system, the output S may be used to control downstream processing, for example, downstream sorting, of a detected particle. In other embodiments, such as where the particle inspection system 11 is a secondary particle inspection system, the output S may be used to monitor/evaluate upstream processing of a detected particle or to further process the particle. In exemplary embodiments, the particle inspection system 11 may include a plurality of detectors. For example, the particle inspection system 11 may include a plurality of detectors included in or operatively coupled directly or indirectly to a same flow-path at a same point/region along the flow-path. In some embodiments, the plurality of detectors may be used to detect a plurality of signals for determining measurements for different particle characteristics at the same point/region along the flow-path. In exemplary embodiments the particle inspection system 11 may process raw data from one or more detectors to obtain the output S. In some embodiments the particle inspection system 11 may include one or more detectors included in or operatively coupled directly or indirectly to a plurality of flow-paths or a same flow-path at a plurality of points/regions along the flow-path. Such detector multitasking may be advantageous for optimal use of space/resources in the particle processing system 10.

With reference still to FIG. 1, in exemplary embodiments, the particle processing system 10 may include or be operatively associated directly or indirectly with a controller 12, for example, for controlling the particle inspection system 11. In exemplary embodiments, the controller 12 may be configured to obtain, for example, a measurement value for a particle characteristic based, for example, on the output S from the particle inspection system 11. In other embodiments the output may include a measurement value for a particle characteristic. The controller 12 may further be configured to analyze the measurement value for the particle characteristic take an action based thereon. For example, the controller 12 may be configured to control downstream processing of a detected particle based on an obtained measurement value for the particle characteristic for the detected particle. In other embodiments, the controller 12 may be used to evaluate an upstream processing of a detected particle and notify a user about and/or adjust, optimize or maintain an operational characteristic of the particle processing system 10 based thereon, for example, if a particle processing error is detected. One of ordinary skill in the art will appreciate that the controller 12 may be implemented in whole or in part via programming associated with a programmable processor, for example, processor 12a. The controller 12 may further include or be associated with a user interface 12b.

According to the present disclosure, the controller 12 may be advantageously be configured to adjust, for example, normalize, calibrate, or standardize, at least a portion of the output S, for example, a measurement value for a particle characteristic. Such adjustment of the output S may advantageously provide a common basis for comparing the output S relative to a second output representative of the same particle or characteristic (for example, for a different particle, different detection region, different flow-path, different particle inspection system, and/or different particle processing system) or for relating the output S relative to an output representative of a different particle characteristic. Moreover, adjusted output representative of a same particle characteristic (for example, for different particles, different detection regions, different flow-paths, different particle inspection systems, and/or different particle processing systems) or representative of a different particle characteristic may be superimposed so as to allow for the combined analysis/processing thereof. This may enable, for example, visualization and identification of particle populations, for example, across multiple flow-paths/channels (for same or different particle processing systems) and/or across multiple particle inspection systems and provide accurate selection of and processing of sub-populations.

Figure 2:
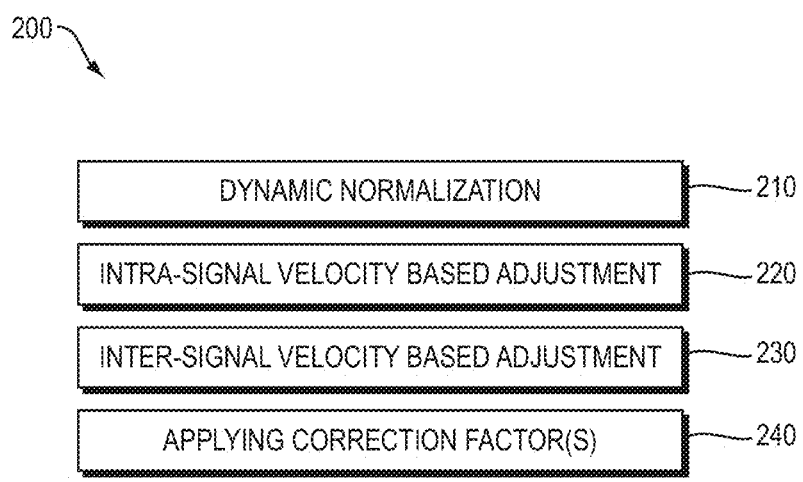
FIG. 2 depicts an exemplary method for adjusting an output of a particle inspection system representative of a particle characteristic for a particle in a flow path of a particle processing system, according to the present disclosure.

With reference now to FIG. 2, an exemplary method 200 for adjusting, for example, normalizing, calibrating or standardizing, an output (for example the output S of FIG. 1) is described. It will be appreciated by one of ordinary skill in the art that the method 200 of FIG. 2 may be implemented in whole or in part via programming associated with a programmable processor (for example, processor 12a of FIG. 1).

In exemplary embodiments, method 200 may include initial steps of dynamic normalization/calibration 210 and velocity-dependent normalization/calibration 220 and 230. Dynamic normalization/calibration 210 may be used, for example, to mitigate instrument-related measurement variability (for example, for measurements by the particle inspection system or between particle inspection systems, or for measurement for different particles, different detection regions, different flow-paths, or different particle processing systems) and background signals and/or noise, such as low frequency signal variations (in optical measurements, low frequency signal power variations may be caused, for example by low frequency laser power fluctuations). In exemplary embodiments, dynamic normalization/calibration 210 may include the following transformation on the output $S_{in}$:

$$S_N = \frac{S_{in}}{S_{Av}} N,$$

where $S_N$ is the output after dynamic normalization/calibration,
where $$S_{Av} = \frac{\sum_{k}^{k+M-1} S_{in}}{M},$$

and
where N and M are constants used to fine tune the normalization/calibration efficacy and end points.

Dynamic normalization/calibration 210 may advantageously be switched off/bypassed whenever a particle is detected (so as to maintain maximum signal resolution). In exemplary embodiments, dynamic normalization/calibration 210 may not be necessary, for example, if the measurement instrument (e.g. illumination laser and/or detector) is of sufficiently low noise.

Velocity based adjustment 220 and 230 may be used to minimize output variability due to differences in particle velocity (for example, for measurements by the particle inspection system or between particle inspection systems, or for measurement for different particles, different detection regions, different flow-paths, or different particle processing systems). Velocity based adjustment may be applied to minimize intra-signal variability (220) due to differences in particle velocity and/or inter-signal variability (230) due to differences in particle velocity. Thus, velocity based adjustment may advantageously adjust the output, for example, adjust a measurement value for a particle characteristic as determined by area, height, slope, or other features of a particle pulse in the output).

In exemplary embodiments, intra-signal velocity based adjustment 220 may be applied by adjusting, for example, particle pulse area measurement ($A_{in}$) by a factor of:

$$A_N = \frac{v}{\bar{v}} A_{in},$$

where $A_N$ is the adjusted particle pulse area,
where $v$ is the particle velocity, and
where $\bar{v}$ is an average particle velocity (for example, a running average of particle velocity).

In other exemplary embodiments, inter-signal velocity based adjustment 230 (also referred to as common velocity normalization/calibration) may be applied by adjusting, for example, normalizing, calibrating or standardizing, particle pulse area ($A_{in}$) relative to a common velocity ($v_C$):

$$A_C = \frac{\bar{v}}{v_C} A_N = \frac{v}{\bar{v}} \frac{\bar{v}}{v_C} A_{in} = \frac{v}{v_C} A_{in},$$

where $A_C$ is the particle pulse area adjusted relative to the common velocity ($v_C$).

In exemplary embodiments, velocity based adjustment may not be necessary, for example, where velocity variations are negligible or where the impact of velocity variations on the signal is negligible.

With reference still to FIG. 2, at step 240 one or more correction factors may be applied to adjust, for example, normalize calibrate or standardize, an output representative of a particle characteristic, for example a measurement value for a particle characteristic. The one or more correction factors may advantageously be determined using one or more calibration particles as is described in greater with respect in FIG. 3. In exemplary embodiments, the one or more correction factors may be applied in real time, for example, using a matrix mechanism such as described herein. In exemplary embodiments, both raw and adjusted outputs representative of a particle characteristic may be obtained for further analysis and/or processing. Adjustment of the output may advantageously provide a common basis for comparing/analyzing the output, for example, with respect to a second output for the same or a relatable particle charactereristic.

In exemplary embodiments, an output may be representative of a particle characteristic, for example, may include measurement values for a particle characteristic, for a plurality of particles. Thus, for example, distributions of measurement values for the particle characteristic for a population of particles may be generated, for example, for different particle inspection systems. In such embodiments, correction factors, may be determined, for example, by identifying and correlating related regions in the distributions. A suitably trained neural-network or other adaptive learning system could be used to facilitate such identification and correlation.

Figure 3:
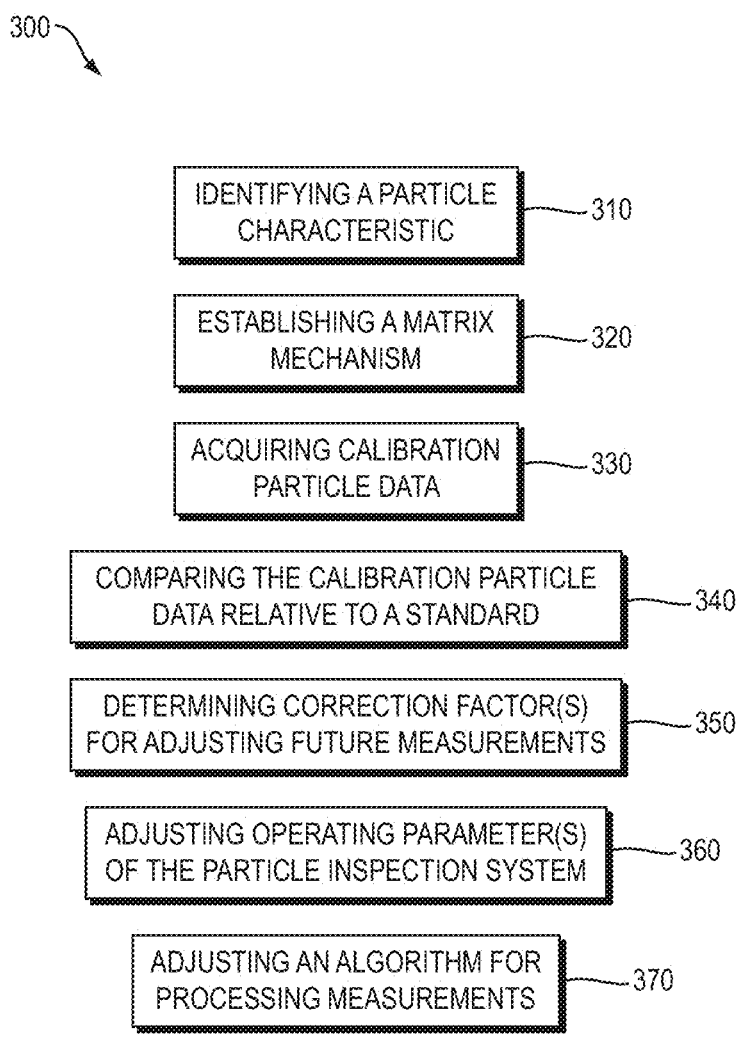
FIG. 3 depicts an exemplary method for facilitating adjustment of measurement detection and/or processing of a particle characteristic by particle inspection system in a particle processing system, according to the present disclosure.

With reference to FIG. 3, an exemplary method 300 for facilitating adjustment of measurement detection and/or processing of a particle characteristic by particle inspection system (for example the particle inspection system 11 of FIG. 1) in a particle processing system is depicted. At step 310 a particle characteristic, a particle characteristic which is detectable by the particle inspection system, is identified. The identified particle characteristic may advantageously be relevant to the processing, for example, the sorting of particles, by the particle processing system. At step 320, a matrix mechanism may be established, for example, in flow-channel signal processing electronics. The matrix mechanism may advantageously allow for real-time application of correction factors to an output representative of the particle characteristic. With reference now to FIGS. 18A-18B (note that FIG. 18B is a continuation of the table in FIG. 18A), exemplary correction factors matrixes are depicted. More particularly, each particle inspection system (channel numbers 1-8) may include a matrix of constants that including offsets (produced by the electronics and the optical background) and adjustment constants.

With reference again to FIG. 3, at step 330, data may be acquired, for example, by detecting with the particle inspection system an output representative of the particle characteristic for one or more calibration particles. It is noted that calibration particles may be any particles and that calibration particles are note limited to the specific examples thereof presented herein. In exemplary embodiments, the calibration particles may be selected to include identifiable populations with respect to the particle characteristic. To illustrate, in an exemplary embodiments, florescence brightness (as may be characterized by signal strength for a florescence detector) may be relevant to particle processing. Thus, a set of calibration particles with known florescence brightness or known relative fluorescence brightness may be identified. In exemplary embodiments, these particles may include, non-fluorescent (blank or negative) particles, for example, cells, (for example, to help determine the signal pedestal) and at least one easily identifiable fluorescent (positive) particle population, preferably with easily distinguishable cluster of measurement values above pedestal. At step 340 the detected output representative of the particle characteristic for the one or more calibration particles may be compared relative to a standard. For example, the detected fluorescence brightness calibration particle(s) may be compared relative to the known fluorescence brightness for the calibration particle(s).

Figure 4:
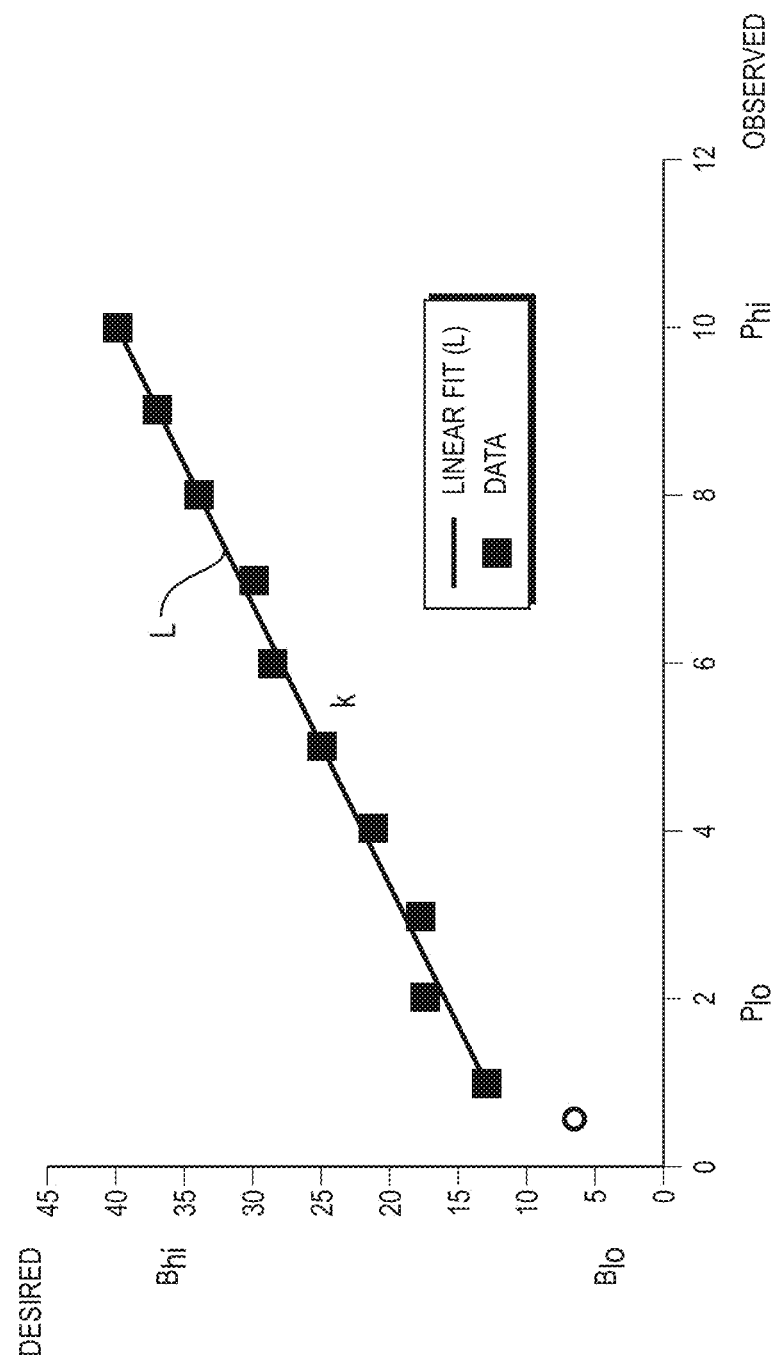
FIG. 4 depicts using a fitting function to correlate an output of a particle inspection system representative of a particle characteristic for a plurality of calibration particles in a flow path of a particle processing system relative to a standard, according to the present disclosure.

In exemplary embodiments, at step 350 one or more correction factors for adjusting for example, normalizing, calibrating or standardizing, future measurement or detection of the particle characteristic may be determined. In some embodiments the correction factors may be determined by using a fitting function such as a linear or other regression algorithm to relate detected measurement values for the particle characteristic for one or more calibration particles to a standard. In exemplary embodiments, the standard may be selected so as to optimize dynamic range and resolution for measurement or detection of the particle characteristic, for example, for a target population of particles. Thus, for example, in the case of fluorescence, measurement or detection of fluorescence brightness for the calibration particles may be correlated with respect to known/desired brightness, or known/desired relative brightness for the calibration particle(s). In exemplary embodiments, a cluster of measurement values for the characteristic for a plurality of calibration particles may be used to identify a population of calibration particles. Thus, one or more clusters of measurement values may be identified and correlated with respect to known/desired brightness or known/desired relative brightness for the corresponding calibration particle population. In exemplary embodiments, a pattern of clusters may be used such that it is quickly identifiable to facilitate correlation to a standard. The cluster pattern may be established by selecting a plurality of clusters with a known relative brightness between themselves. Within reason, the greater the number of clusters the more unique the pattern will be. In exemplary embodiments, such as depicted in FIG. 4, this calculation may be based on a linear fit L for observed versus known/desired data for two or more clusters resulting in a normalization/calibration constant (slope k) and pedestal (in this case, optical background offset o). Note that in the case wherein the particle characteristic is multi-dimensional a multi-dimensional envelope may be applied. This would work well, for example, where the particle characteristic is the overall spectral signature of a particle. In some embodiments, the choice of calibration particles may be used to define the range and the resolution of the normalized data. In order to reduce errors in cluster detection, a specially binned linear-log histogram may be filled, such that greater measurement values, for example, high brightness peaks are effectively compressed without changing the underlying data. A cluster finding algorithm may further be applied to eliminate false peaks. In exemplary embodiments, calculated correction factors may be evaluated by a series of tests, for example, to provide a quality metric for the calibration procedure that can then be used as a part of an automatic validation tool. Feedback may also be obtained for the quality of clusters/peaks used to determine the correction factors. Exemplary tests may include but are not limited to proximity tests (outlier detection), and threshold tests (threshold number of channels/spectral measurements which are within or outside of acceptable limits) or other tests.

Figure 14:
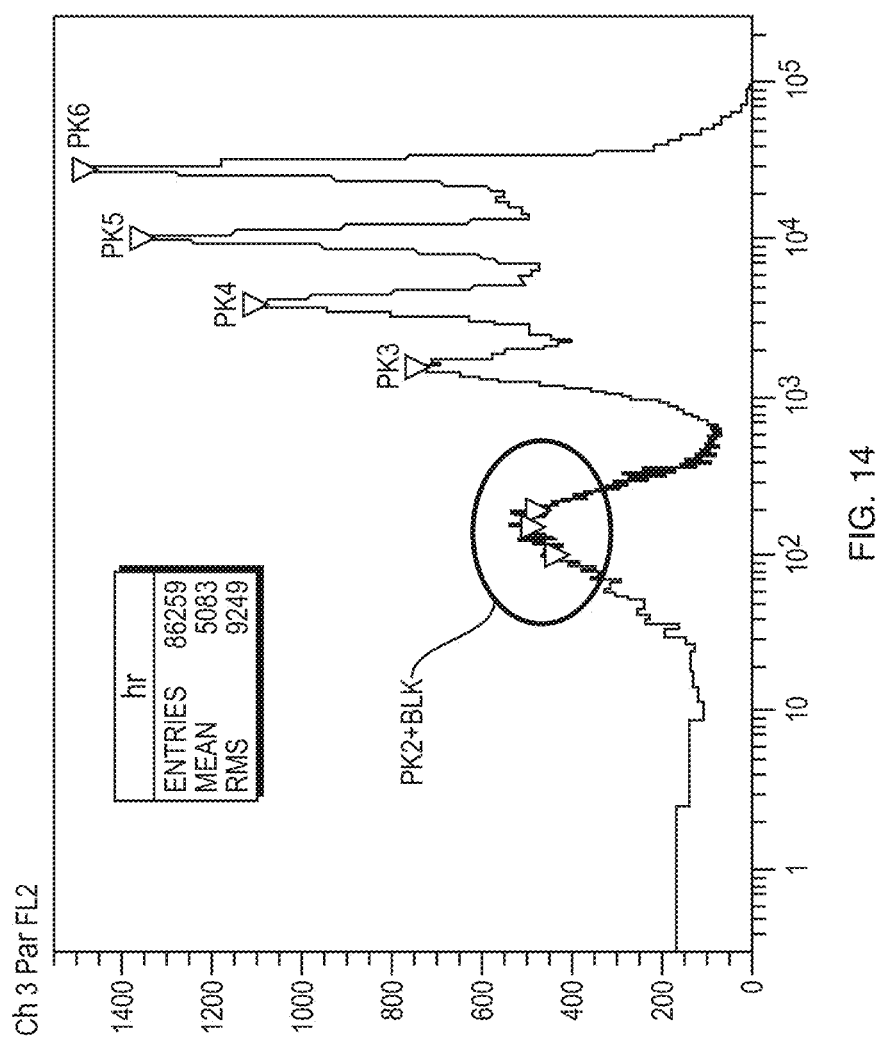
FIG. 14 depicts exemplary peak/cluster detection, according to the present disclosure.

With reference to FIG. 14, exemplary peak/cluster detection is depicted for an output representative of a particle characteristic (fluorescence FL3) for a population of calibration particles including a sub-population of blank particles and sup-populations of ultra-rainbow particles (clusters/peaks 2, 3, 4, 5 and 6 ). Notably, cluster/peak 2 is not properly identified due to its proximity to the pedestal as determined by the blank particle peak BLK. Thus, cluster/peak 2 may be advantageously discarded when calculating correction factors.

With reference again to FIG. 3, in exemplary embodiments, at step 360 calibration particle data may be used to adjust one or more operational parameters of the particle inspection system, for example, to adjust measurement or detection of the particle characteristic by of the particle inspection system, for example relative to a standard. More particularly, operational parameters of the particle inspection system such as laser power, photodetector voltage or gain, flow rate or the like, may be adjusted based on deviations of the output/signal representative of the particle characteristic for the one or more calibration particles relative to a standard. This may be an iterative process, for example, to reduce/minimize such deviations.

In exemplary embodiments, at step 370, calibration particle data may be used to adjust an algorithm for processing an output representative of a particle characteristic. Thus, in some embodiments, a standard algorithm, for example, an algorithm originally configured for processing an output conforming to a standard, may be adjusted based on deviations of the output for the one more calibration particles relative to the standard. In this way, a standard algorithm may be tailored, for example, for a particular particle inspection system.

Figures 16, 17:
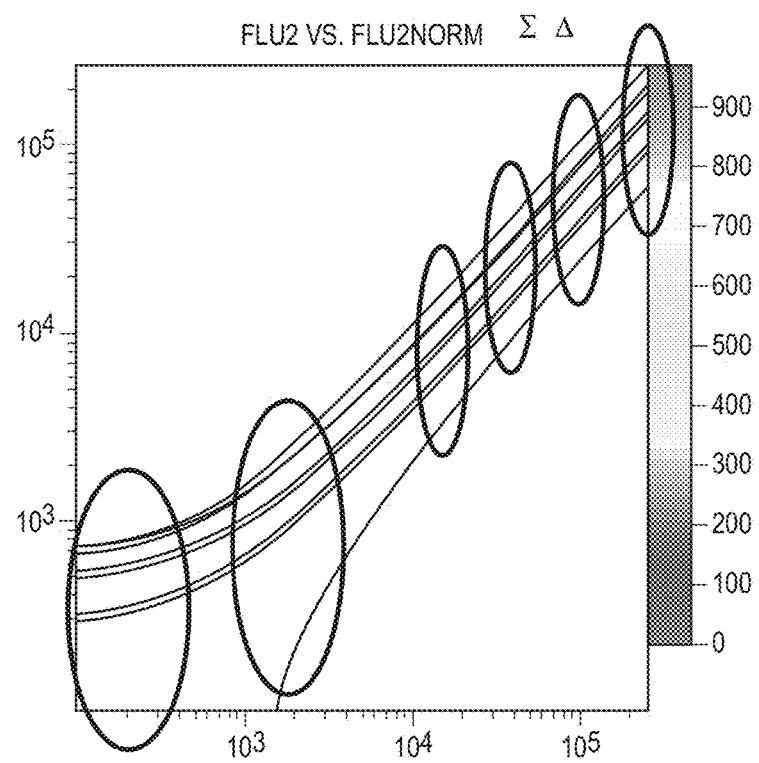
FIG. 16 depicts the relationship between the raw and adjusted data of FIG. 15, according to the present disclosure.
FIG. 17 depicts an exemplary brightness table for calibration particles, according to the present disclosure.

In considering calibration particles for multi-spectral detection, and in particular, multi-spectral fluorescence detection, it may be useful to consider that some fluorescent markers have a relatively wide spectrum. These markers are susceptible to being misidentified when their signal is examined across two different spectral ranges. A suitable choice of calibration particles and matrix inversion techniques for the two-dimensional correction factor matrix compensates by enabling identification of individual markers per a combined spectral signature. With reference to FIG. 17, an exemplary brightness table for calibration particles (blank and URp2-URp6) is depicted. Notably, particular populations of calibration particles have been selected to set the dynamic range and resolution for each of fluorescence measurements FLU1-FLU4.

Figure 5:
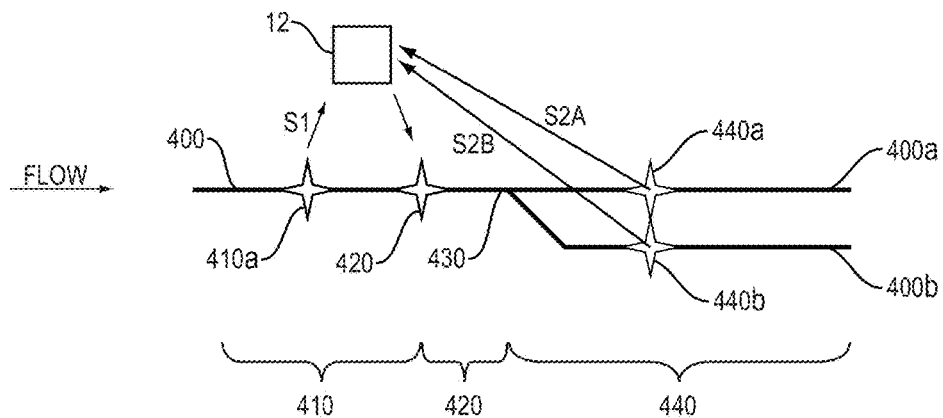
FIG. 5 depicts an exemplary flow-path for a particle processing system, according to the present disclosure.

With reference now to FIG. 5 an exemplary flow-path 400 for a particle processing system (for example, the particle processing system 10 of FIG. 1) is depicted. As depicted, the flow-path 400 is a branched flow-path for particle sorting operations. In exemplary embodiments, the flow-path 400 may be a flow-channel, for example, a microchannel, defined in a substrate, for example, of a microfluidic chip. The flow-path 400 may be configured to receive a stream of particles suspended in a carrier fluid in a flow direction. The flow-path 400 may include a primary measurement/detection region 410, a processing/sorting region 420 in proximity to the primary measurement/detection region 410 and a branch point 430 downstream of the processing/sorting region 420 where the flow-path 400 branches into a plurality of output branches 400a and 400b and a secondary measurement/detection region 440 downstream of the processing/sorting region 420, for example, downstream of the branch point 430 and along the output branches 400a and 400b of the flow-path 400.

The flow-path 400 may include or be operatively associated with a primary particle inspection system 410a for measuring or detecting a particle at the primary measurement/detection region 410. The primary particle inspection system 410a may be used to obtain an output $S_1$ representative of a particle characteristic for the particle which may serve as criteria for processing/sorting the particle at the processing/sorting region 420. In some embodiments, the primary particle inspection system 410a may detect particle velocity, for example, for controlling timing on a particle-by-particle basis. Exemplary apparatus, systems and methods for measuring particle velocity are addressed in U.S. Pat. Nos. 6,976,590 and 7,569,788. In exemplary embodiments, the primary particle inspection system 410a may be operatively associated with a controller 12 for receiving and analyzing the output $S_1$. In exemplary embodiments, the controller 12 may be operatively associated with a plurality particle inspection systems and/or a plurality of outputs.

The flow-path 400 may also include or be operatively associated with a particle processing device 420a for selectively processing/sorting particles at the processing/sorting region 420. For example, the particle processing device 420a may selectively sort a particle by deflecting it into one of the output branches 400a and 400b of the flow-path 400. It is noted that while the flow-path 400 depicted in FIG. 5 includes two output branches 400a and 400b, the present disclosure is not limited to such an embodiment. Indeed, in some embodiments the flow-path 400 may include more than two output branches. In exemplary embodiments, the particle processing device 420a may be configured such that deflected particles sort into one of one or more "active" branches of the flow-path 400 and non-deflected particles sort into one of one or more "passive" branches of the flow-path 400. In some embodiments, the particle processing device 420a may include or be operatively coupled directly or indirectly to an actuator. The particle processing device 420a may also include or be operatively associated with a controller for controlling the particle processing device 420a, for example, the same controller 12 as for the primary particle inspection system 410a or a different controller.

In exemplary embodiments, the flow-path may 400 may include or be operatively associated with secondary particle inspection systems 440a and 440b for measuring and/or detecting particles at the secondary measurement/detection region 440. Thus, for example, the secondary particle inspection systems 440a and 440b may produce outputs $S_{2a}$ and $S_{2b}$, each representative of a particle characteristic, for a processed particles in or flowing from a corresponding one of the output branches 400a and 400b. The outputs $S_{2a}$ and $S_{2b}$ may be used, for example, to evaluate upstream processing of detected particles or for further processing of the detected particles. In exemplary embodiments, the secondary particle inspection systems 440a and 140b may be operatively associated with a controller for receiving and analyzing the output $S_{2a}$ and $S_{2b}$, for example, the same controller 12 as for the primary detector 410a or a different controller.

Advantageously, each of the output $S_1$, $S_{2a}$ and $S_{2b}$ for example, measurements of a particle characteristic, may be adjusted, for example, normalized, calibrated or standardized, using the systems, methods and non-transitory storage medium described herein, for example, the methods described with respect to FIGS. 2-3. Thus, for example, where the output $S_1$, $S_{2a}$ and $S_{2b}$ represent a same particle characteristic such as florescence, the output $S_1$, $S_{2a}$ and $S_{2b}$ may be adjusted to allow for inter-relatability. In some embodiments, adjusted output $S_1$, $S_{2a}$ and $S_{2b}$, may be collectively analyzed, visualized and/or evaluated.

Figure 6:
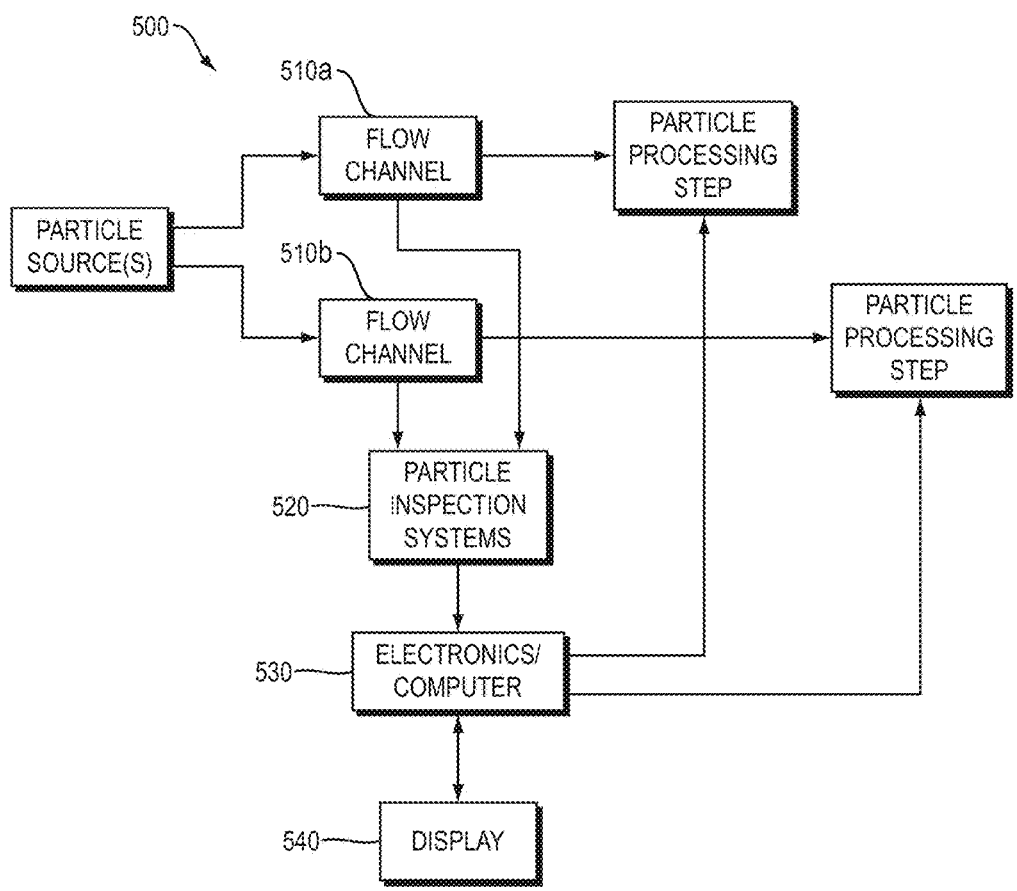
FIG. 6 depicts an exemplary particle processing system according to the present disclosure.
Figure 7:
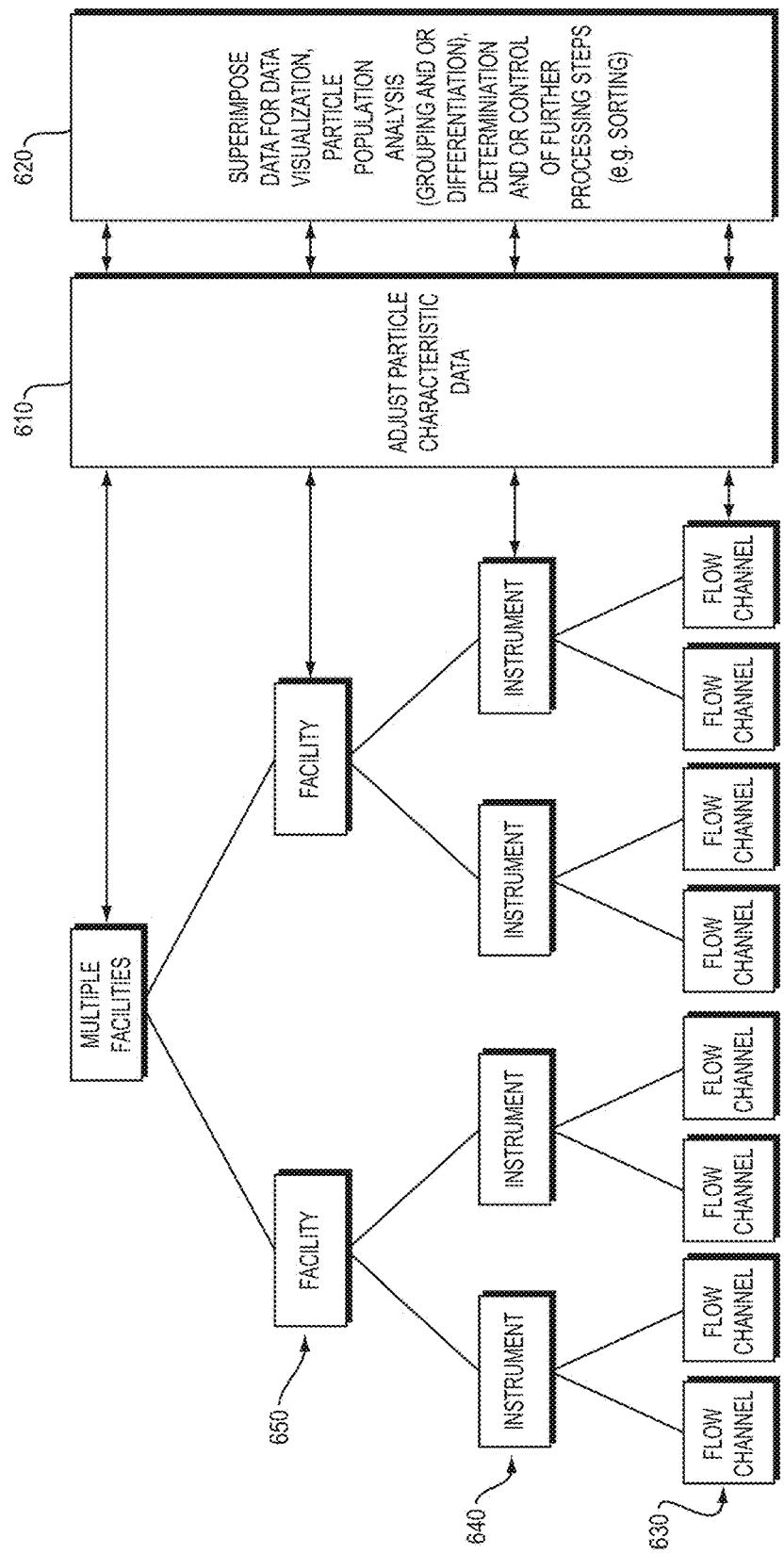
FIG. 7 depicts adjustment and processing of measurements across an exemplary network of particle processing systems, according to the present disclosure.

In exemplary embodiments, such as depicted in FIGS. 6 and 7, the systems, methods and non-transitory storage medium described herein may be applied to superimpose and, in some instances, visualize measurement values for a particle characteristic for different particles, different detection regions, different flow-paths, different particle inspection systems, and/or different particle processing systems. With reference to FIG. 6, an exemplary particle processing system 500 is depicted, including a plurality of flow-channels 510a and 510b. Particles entering the flow-channels 510a and 510b may be measured or detected using one or more particle inspection systems 520. A control system 530 including a computer and/or electronics, may be used to adjust an output representative of a same particle characteristic for each of the flow-channels 510a and 510b, according to the systems, methods and non-transitory storage medium described herein. The adjusted outputs for both flow-channels 510a and 510b may then be superimposed for further analysis and processing. In exemplary embodiments, the superimposed outputs may be displayed on a display 540 to facilitate particle processing (for example, to facilitate selection one or more particle subpopulations for sorting). FIG. 7, depicts the ability to adjust 610 and superimpose 620 (for combined processing/analysis) measurements of a particle characteristic across a plurality flow-paths, for example, flow channels 630, particle processing systems, for example instruments 640, and locations, for example, facilities 650, according to the present disclosure.

Figure 8A:
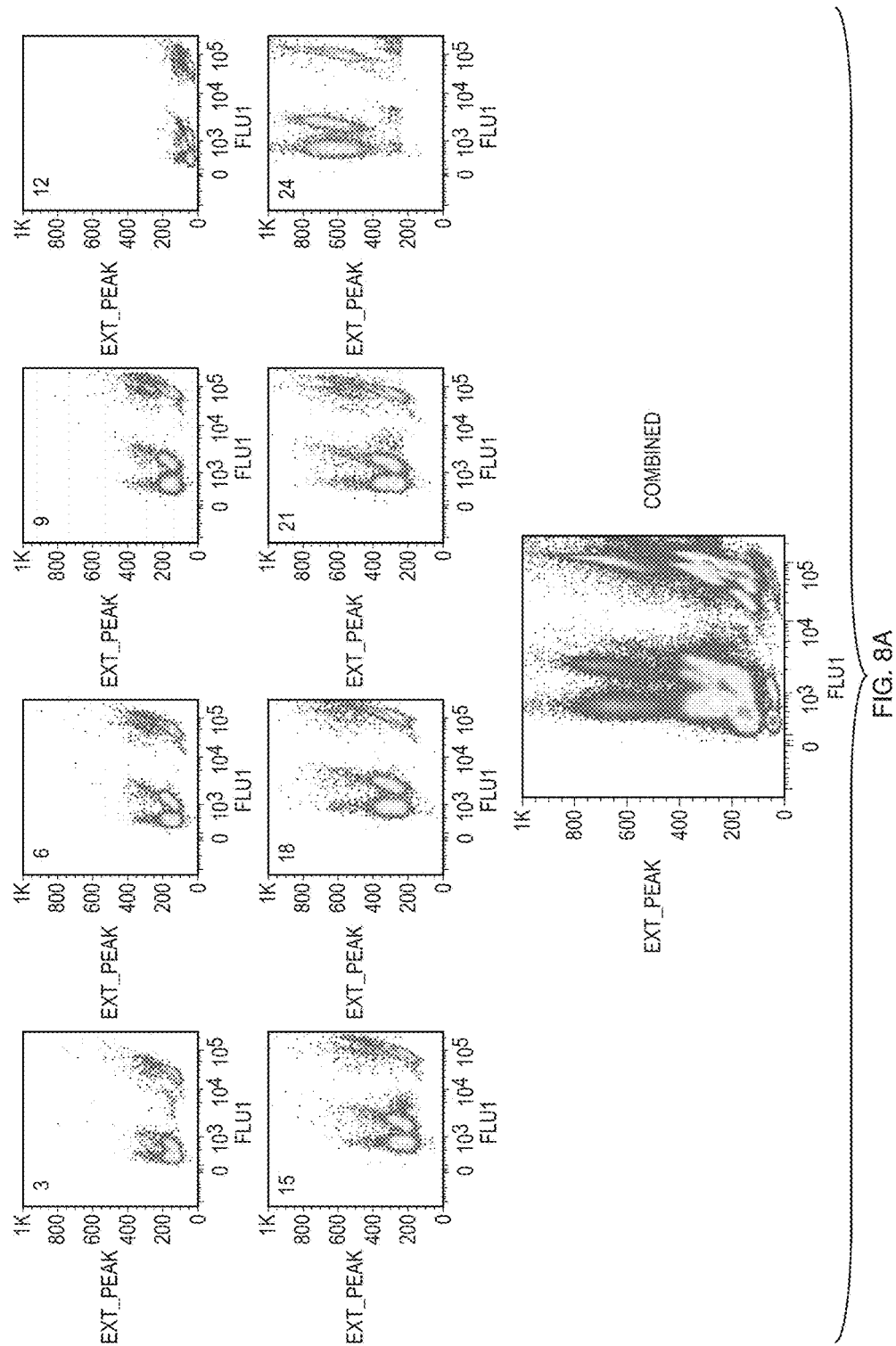

With reference to FIGS. 8A-8B, bivariate plots (light extinction versus fluorescence) are depicted for a plurality of flow-channels individually and in combination before (FIG. 8A) and after (FIG. 8B) output adjustment. The data was obtained for a three-marker particle population including blank, dim positive, and bright positive particles (clusters 801, 802 and 803) as excited by a 532 nm laser and detected using a spectral waveband of 560-600 nm. The combined plots clearly demonstrate the effect and accuracy of adjusting the output representative of fluorescence for each of the flow-channels. Advantageously, after output adjustment, data for multiple flow-channels may be viewed and analyzed, collectively. For example, population statistics may be determined for multiple flow-channels. Moreover, particle sub-populations across multiple flow-channels may be easily and quickly identified, for example, further processing. The determination of particle sub-populations may be automated by applying processing algorithms tailored to the standard for example algorithms for thresholding/grouping relative to normalized measurement values. It will be appreciated, that, in exemplary embodiments, the multiple flow-channels may be in different particle processing systems, and that the different particle processing systems, may be in different geographic locations.

Figure 9A:
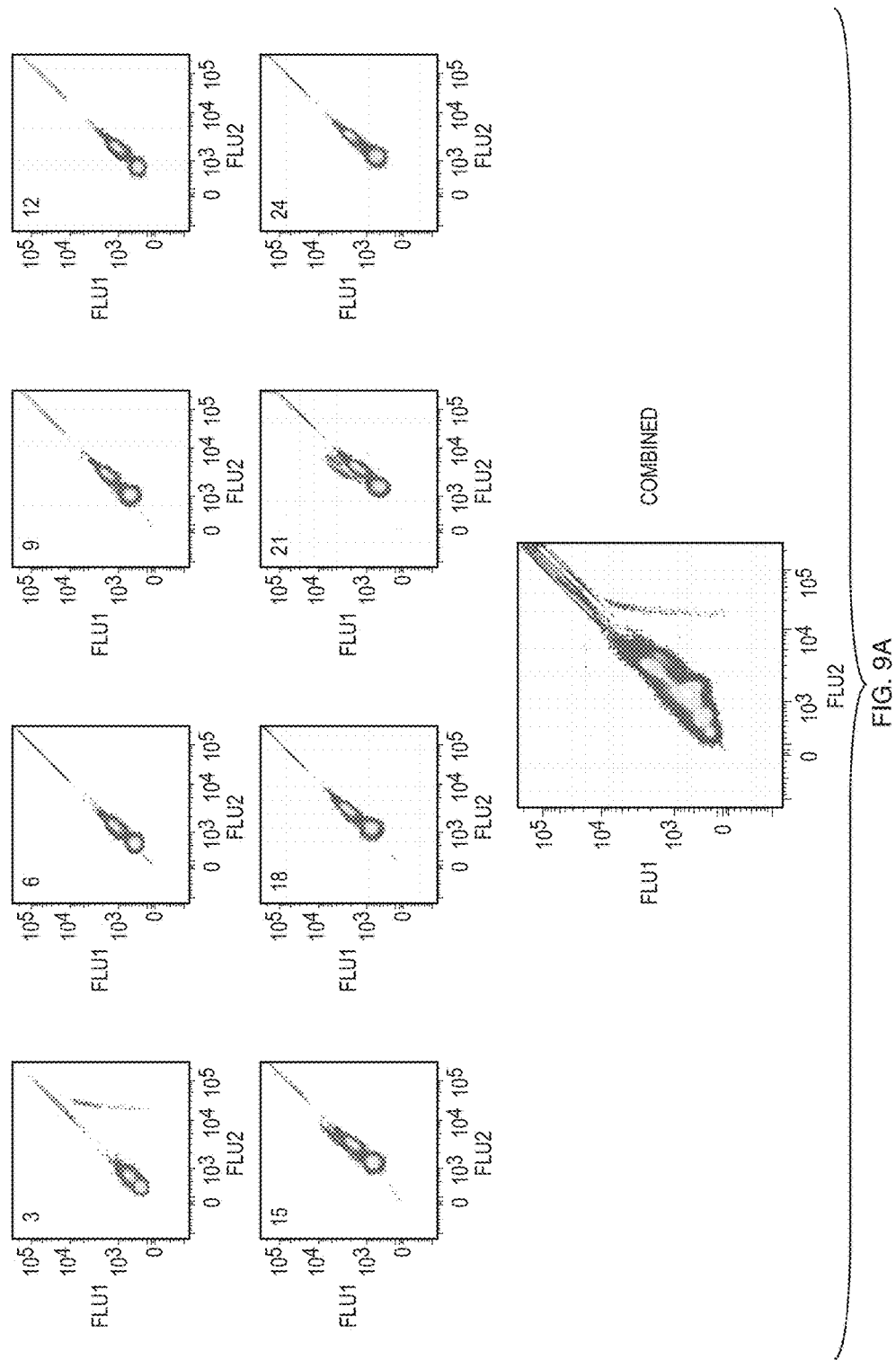
FIGS. 9A-9B depict two-color florescence bivariate plots for a plurality of flow-channels individually and in combination before and after measurement adjustment, according to the present disclosure.
Figure 9B:
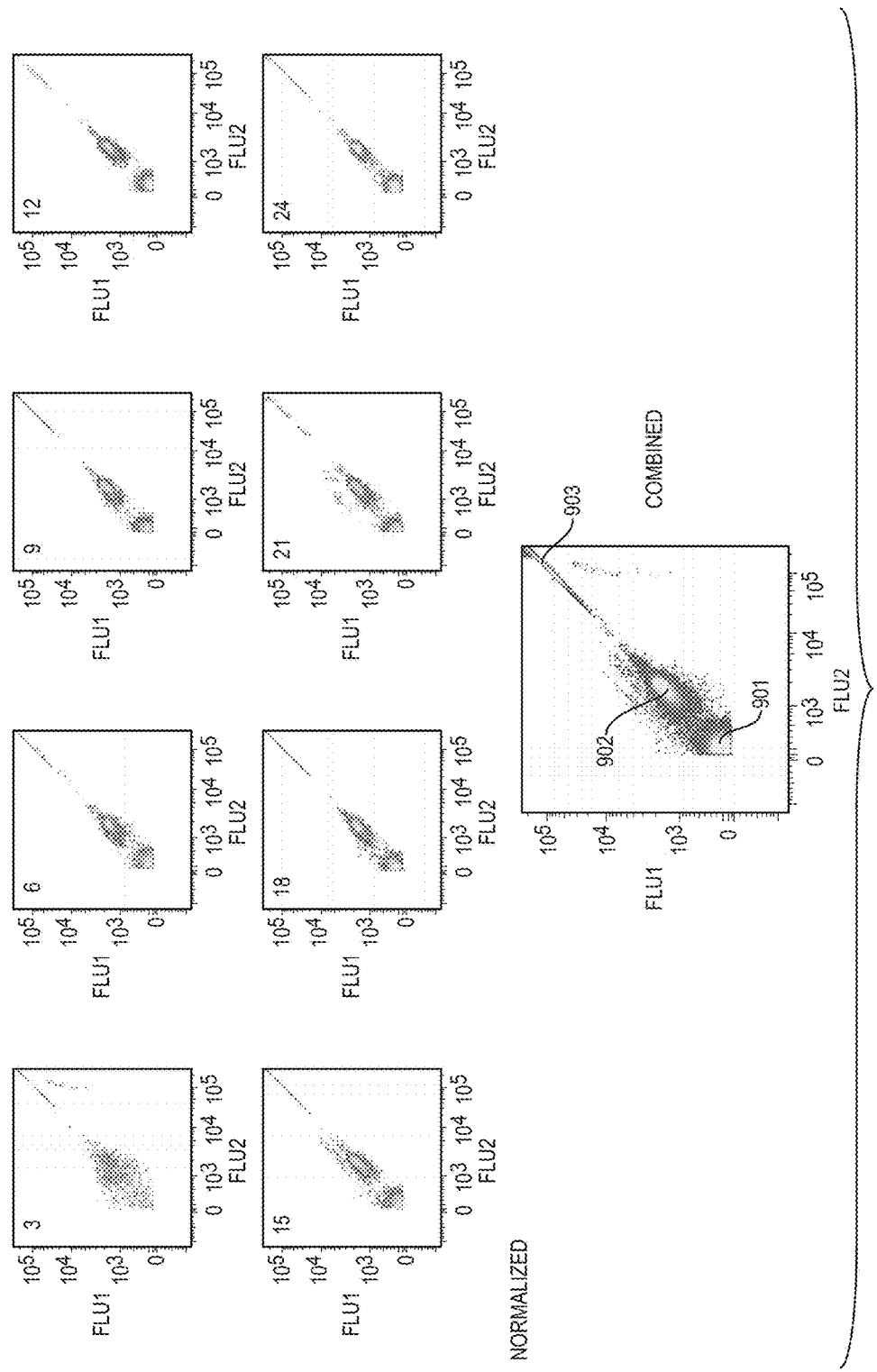

As previously noted, the systems, methods and non-transitory storage medium described herein, may advantageously be applied to measurement or detection of multi-spectral fluorescence. FIGS. 9A-9B depict two-color florescence bivariate plots (fluorescence 1 versus fluorescence 2) for a plurality of flow-channels individually and in combination before (FIG. 9A) and after (FIG. 9B) output adjustment. Once again, the combined plots clearly demonstrate the effect and accuracy of adjusting the output representative of fluorescence 1 and fluorescence 2 for each of the flow-channels. The data was obtained for a three-marker particle population as evidenced by the three population clusters (901, 902 and 903)

Figure 10B:
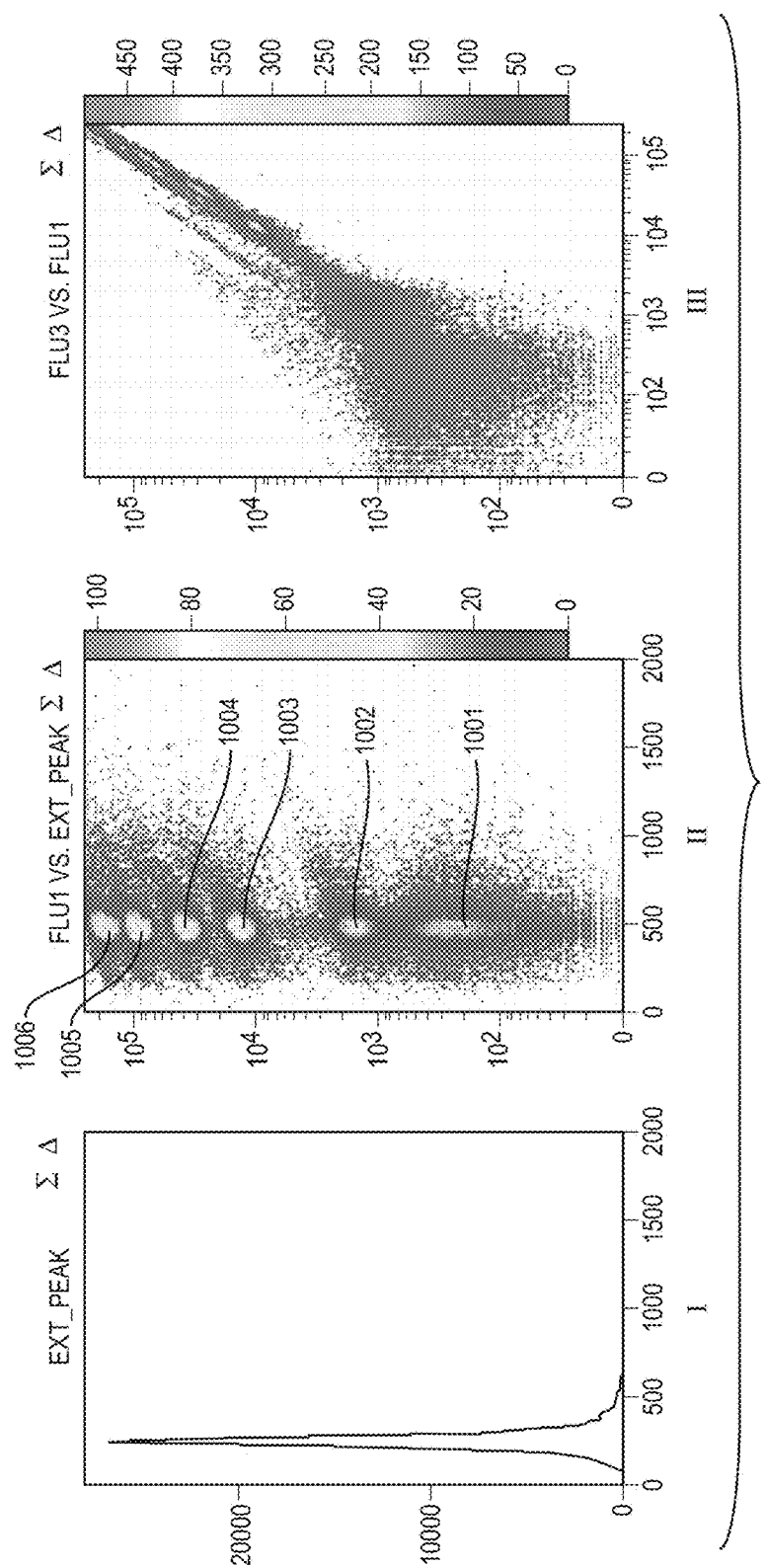

FIGS. 10A-10B depict bivariate plots of (I) light extinction versus particle size, (II) fluorescence versus light extinction, and (III) fluorescence 3 versus fluorescence 1, for a combined plurality of flow-channels before (FIG. 10A) and after (FIG. 10B) output adjustment. The data was obtained for a six-marker population (clusters 1001-1006).

Figure 11:
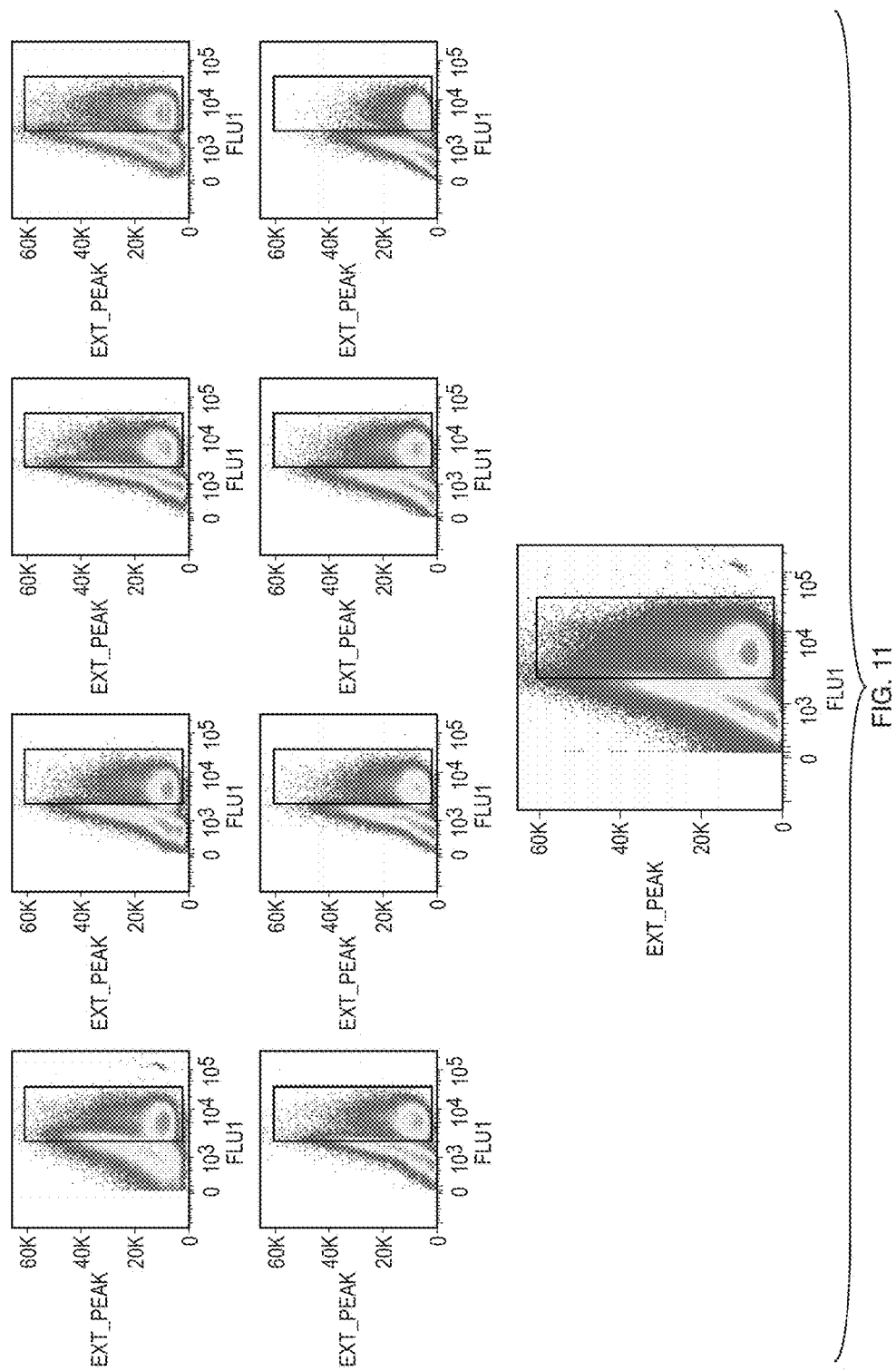
FIG. 11 depicts data for a population of CD-3 labeled cells which is adjusted and combined across multiple flow channels, according to the present disclosure.

As noted above, once correction factors are obtained they may be applied to adjust future measurement or detection of a particle characteristic. In FIG. 11 data for a population of CD-3 labeled cells is adjusted by applying pre-set correction factors (previously determined using calibration particles) and combined across multiple flow channels. This may be particularly useful for calculating/analyzing population statistics and/or identifying/analyzing rare sub-populations, for example for further processing steps such as cell sorting, enrichment, or purification.

Figures 15A, 15B:
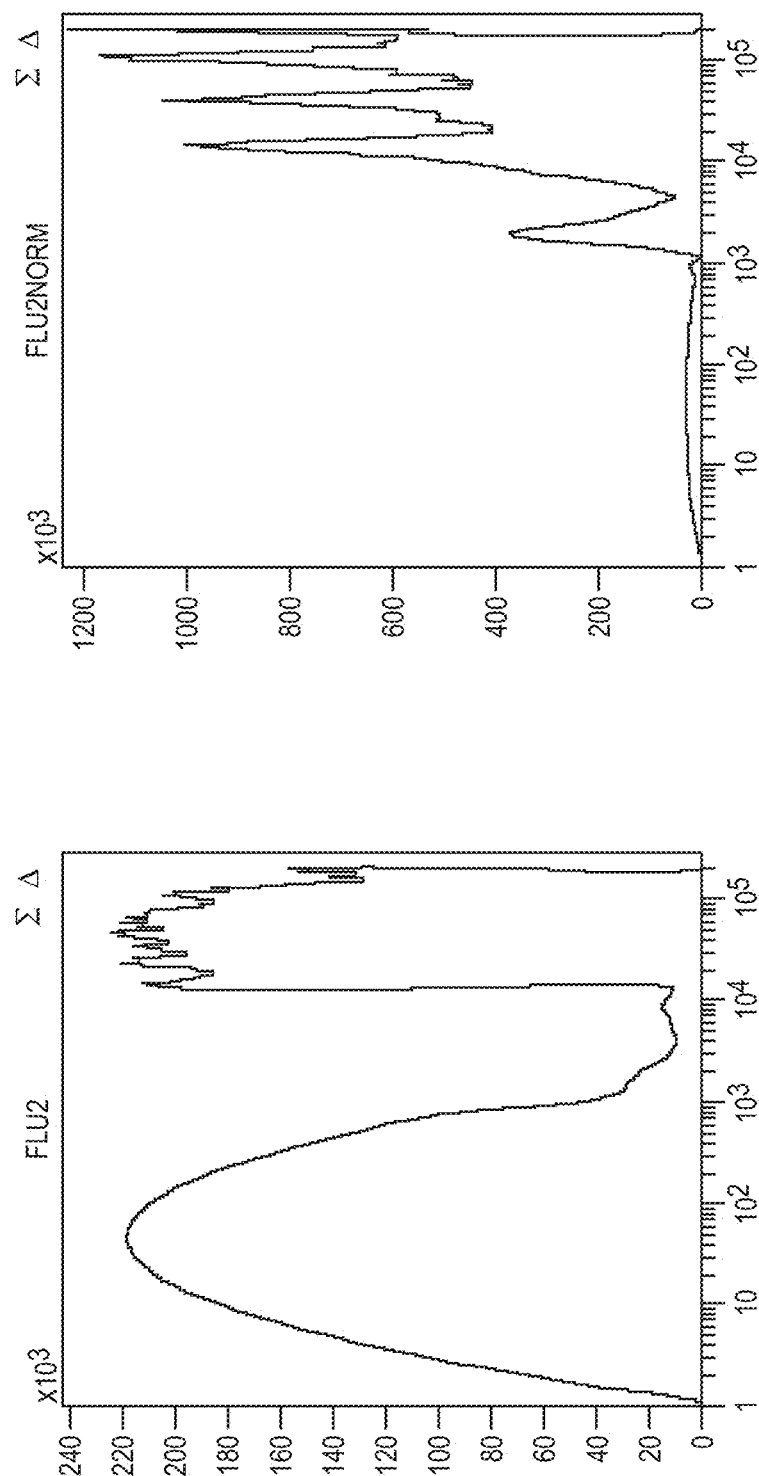
FIGS. 15A-15B depict fluorescence versus particle size for a combined plurality of output channels before and after measurement adjustment, according to the present disclosure.

Referring now to FIGS. 15A-15B bivariate plots (fluorescence versus particle size) are depicted for a combined plurality of output channels before (FIG. 15A—FLU2) and after (FIG. 15B—FLU2 normalized) output adjustment. Pre-adjustment it is very difficult to distinguish between clusters/peaks. Post adjustment, measurement values for particles with corresponding brightness converge resulting in clearly identifiable clusters/peaks. Referring now to FIG. 16, the relationship between the raw and adjusted data of FIG. 15 is depicted. More particularly, FLU2 (y axis) is plotted in relation to against FLU2 normalized (x axis). The circled regions represent shades of the same population (e.g., as determined by particle size) resulting from the different channels lining up in the x-axis.

Detectors, may be any detector for measuring or detecting a particle including but not limited to optical detectors, electrical detectors, magnetic detectors, acoustic detectors, electromagnetic wave detectors and the like. Detectors may advantageously be used to detect a particle or an absence of a particle in a flow-channel/flow-path. Detectors may further be used to detect one or more particle characteristics, for example, for facilitating identification/classification of particles.

Exemplary optical detector configurations are provided in FIGS. 10-13. of U.S. Application No. 61/429,339, filed Jan. 3, 2011, entitled "Method and Apparatus for Monitoring and Optimizing Particle Sorting," the contents of which are incorporated herein to the extent that they are not inconsistent with the present disclosure.

Detector configurations are not limited to optical configurations. Indeed, other detection approaches may be applied instead of or in conjunction with optical means. These approaches may include but are not limited to (i) passive or active electrical detection including but not limited to conductance, capacitance, RF field monitoring through devices fabricated on the microchip, or located off-chip near channels of interest (ii) magnetic detection, such as using a Hall-effect device or other field probes located in the proximity of flow-channels and (iii) acoustic detection such as ultrasound absorption, reflection, scatter or the like using on-board or remote devices, (iv) chemical or molecular detection devices including but not limited to devices such as mass spectroscopy devices.

In exemplary embodiments, a particle may be detected by an analog level, for example by surpassing (going above or below) a threshold which produces a detectable voltage change. The signal may be used to characterize, identify or count the particle.

Temporal information may be used to determine the velocity of the particle, the time elapsed from the detection of the particle at another location, the expected time that the particle will reach a selected position, or the like.

In exemplary embodiments, conductive traces may be used to form an electrode array across or along one or more flow-paths where the absence or presence of a particle adjusts the conductivity or other electrical measurement, for example, capacitance, resistance, inductance of the fluid path between any electrode pair. The conductive traces may be formed on one substrate of a microfluidic chip prior to fusing a second substrate to provide contact with flow-path. As a particle flows near or between electrodes, the conductivity of electricity of the electrical circuit may change and be detected with appropriate electronic processing tools such as an analog current meter or a computer. An exemplary electrode array is described with respect to FIGS. 14 and 15 of U.S. Application No. 61/429,339.

Detector configurations and approaches described may be applied for both modular and integrated embodiments of a particle processing system. It will be appreciated by one of ordinary skill in the art that a particle characteristic may be measured using data from any combination of detector configurations. Indeed, the use of multiple parameter detection and/or multi-dimensional characteristics may advantageously enable finer detection of subpopulations of particles.

It is explicitly contemplated that the systems and methods presented herein may include one or more programmable processing units having associated therewith executable instructions held on one or more computer readable medium, RAM, ROM, hard drive, and/or hardware. In exemplary embodiments, the hardware, firmware and/or executable code may be provided, for example, as upgrade module(s) for use in conjunction with existing infrastructure (for example, existing devices/processing units). Hardware may, for example, include components and/or logic circuitry for executing the embodiments taught herein as a computing process.

Displays and/or other feedback means may also be included to convey detected/processed data, for example adjusted output representative of a particle characteristic. The display and/or other feedback means may be stand-alone or may be included as one or more components/modules of the processing unit(s). In exemplary embodiments, the display and/or other feedback means may be used to facilitate selection of one or more particle populations/sub-populations for processing.

The actual software code or control hardware which may be used to implement some of the present embodiments is not intended to limit the scope of such embodiments. For example, certain aspects of the embodiments described herein may be implemented in code using any suitable programming language type such as, for example, assembly code, C, C# or C++ using, for example, conventional or object-oriented programming techniques. Such code is stored or held on any type of suitable non-transitory computer-readable medium or media such as, for example, a magnetic or optical storage medium.

As used herein, a "processor," "processing unit," "computer" or "computer system" may be, for example, a wireless or wire line variety of a microcomputer, minicomputer, server, mainframe, laptop, personal data assistant (PDA), wireless e-mail device (for example, "BlackBerry," "Android" or "Apple," trade-designated devices), cellular phone, pager, processor, fax machine, scanner, or any other programmable device configured to transmit and receive data over a network. Computer systems disclosed herein may include memory for storing certain software applications used in obtaining, processing and communicating data. It can be appreciated that such memory may be internal or external to the disclosed embodiments. The memory may also include non-transitory storage medium for storing software, including a hard disk, an optical disk, floppy disk, ROM (read only memory), RAM (random access memory), PROM (programmable ROM), EEPROM (electrically erasable PROM), flash memory storage devices, or the like.

Figure 12:
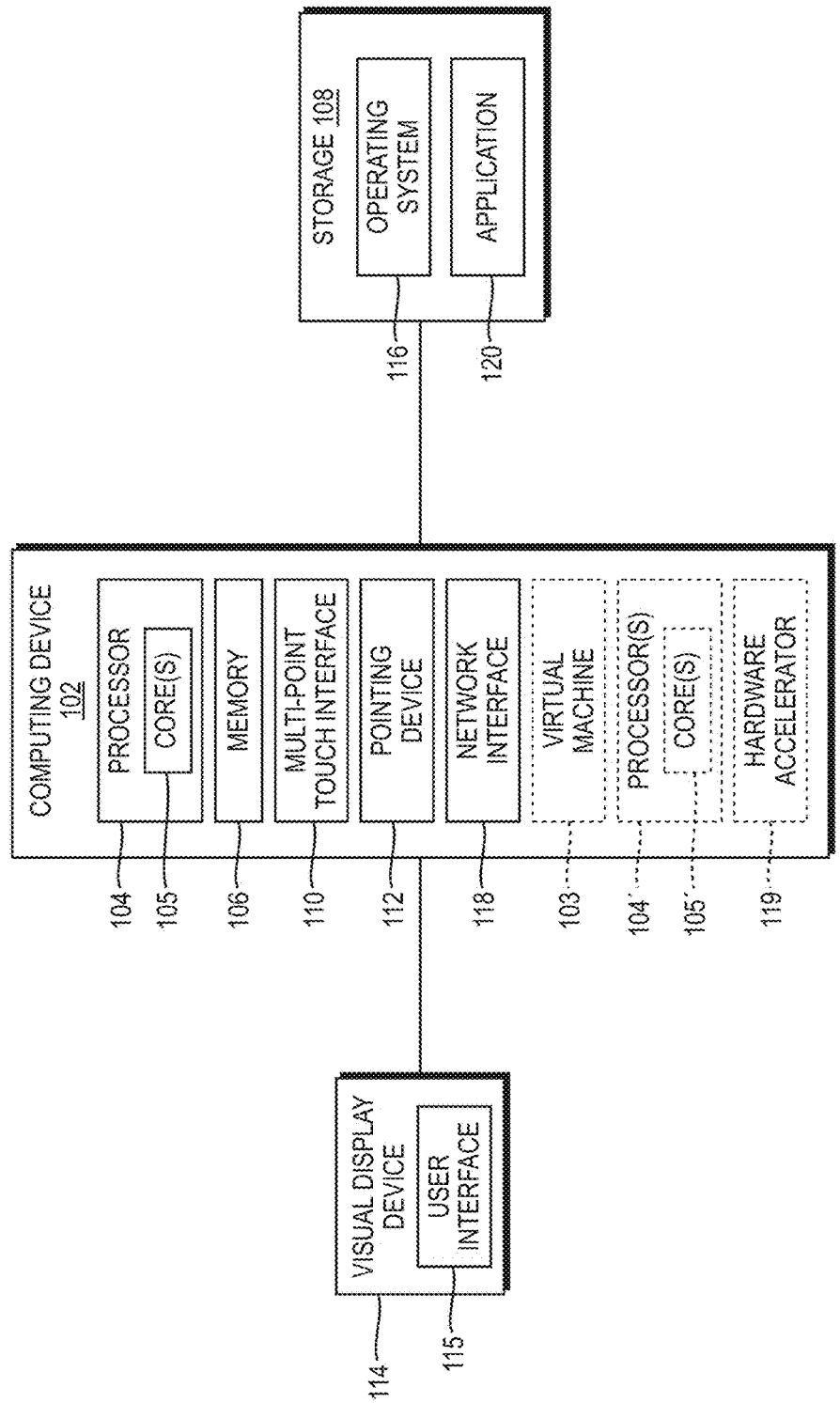
FIG. 12 depicts an exemplary computing environment, according to the present disclosure.

Referring now to FIG. 12 an exemplary computing environment suitable for practicing exemplary embodiments is depicted. The environment may include a computing device 102 which includes one or more media for storing one or more computer-executable instructions or code for implementing exemplary embodiments. For example, memory 106 included in the computing device 102 may store computer-executable instructions or software, for example instructions for implementing and processing every module of the application 120.

The computing device 102 is one example of the controller 12 depicted in FIG. 1. The computing device 102 also includes processor 104, and, one or more processor(s) 104' for executing software stored in the memory 106, and other programs for controlling system hardware. Processor 104 and processor(s) 104' each can be a single core processor or multiple core (105 and 105') processor. Virtualization can be employed in computing device 102 so that infrastructure and resources in the computing device can be shared dynamically. Virtualized processors may also be used with application 120 and other software in storage 108. A virtual machine 103 can be provided to handle a process running on multiple processors so that the process appears to be using one computing resource rather than multiple. Multiple virtual machines can also be used with one processor. Other computing resources, such as field-programmable gate arrays (FPGA), application specific integrated circuit (ASIC), digital signal processor (DSP), Graphics Processing Unit (GPU), and general-purpose processor (GPP), may also be used for executing code and/or software. A hardware accelerator 119, such as implemented in an ASIC, FPGA, or the like, can additionally be used to speed up the general processing rate of the computing device 102.

The memory 106 may comprise a computer system memory or random access memory, such as DRAM, SRAM, EDO RAM, or the like. The memory 106 may comprise other types of memory as well, or combinations thereof. A user may interact with the computing device 102 through a visual display device 114, such as a computer monitor, which may display one or more user interfaces 115. The visual display device 114 may also display other aspects or elements of exemplary embodiments, for example, adjusted measurement values for a particle characteristic. The computing device 102 may include other I/O devices such a keyboard or a multiple-point touch interface 110 and a pointing device 112, for example a mouse, for receiving input from a user. The keyboard 110 and the pointing device 112 may be connected to the visual display device 114. The computing device 102 may include other suitable conventional I/O peripherals. The computing device 102 may further comprise a storage device 108, such as a hard-drive, CD-ROM, or other storage medium for storing an operating system 116 and other programs, for example, a program 120 including computer executable instructions for, calculating correction factors and/or adjusting output.

The computing device 102 may include a network interface 118 to interface to a Local Area Network (LAN), Wide Area Network (WAN) or the Internet through a variety of connections including, but not limited to, standard telephone lines, LAN or WAN links (for example, 802.11, T1, T3, 56 kb, X.25), broadband connections (for example, ISDN, Frame Relay, ATM), wireless connections, controller area network (CAN), or some combination of any or all of the above. The network interface 118 may comprise a built-in network adapter, network interface card, PCMCIA network card, card bus network adapter, wireless network adapter, USB network adapter, modem or any other device suitable for interfacing the computing device 102 to any type of network capable of communication and performing the operations described herein. Moreover, the computing device 102 may be any computer system such as a workstation, desktop computer, server, laptop, handheld computer or other form of computing or telecommunications device that is capable of communication and that has sufficient processor power and memory capacity to perform the operations described herein.

The computing device 102 can be running any operating system such as any of the versions of the Microsoft® Windows® operating systems, the different releases of the Unix and Linux operating systems, any version of the MacOS® for Macintosh computers, any embedded operating system, any real-time operating system, any open source operating system, any proprietary operating system, any operating systems for mobile computing devices, or any other operating system capable of running on the computing device and performing the operations described herein. The operating system may be running in native mode or emulated mode.

Figure 13:
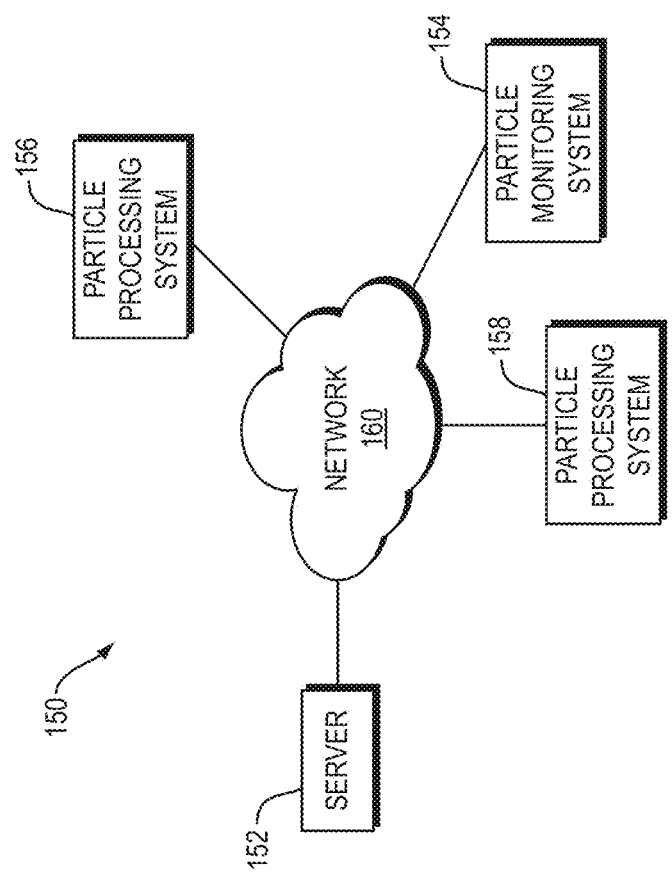
FIG. 13 depicts an exemplary network environment, according to the present disclosure.

FIG. 13 illustrates an exemplary network environment 150 suitable for a distributed implementation of exemplary embodiments. The network environment 150 may include a server 152 coupled relative to a network 160. The server 152 may include an application 120", which may include computer readable instructions for carrying out the methods disclosed herein. The network environment 150 may further includes one or more particle processing systems, for example particle processing systems 156 and 158, coupled, relative to the network 160. Particle processing systems 156 and 158 may be particle processing systems such as described above with respect to FIGS. 1 and 5, and may include an application 120 which may include computer readable instructions for carrying out the methods disclosed herein. The particle processing systems 156 and 158 may also be located at geographically remote locations. The network environment 150 may also include a particle monitoring system 154 coupled relative to the network 160 for receiving data from the one or more particle processing systems across the network 160. The particle monitoring system may include an application 120' which may include computer readable instructions for carrying out the methods disclosed herein. The server 152, particle monitoring system 154 and/or particle processing systems 156 and/or 158 may be implemented at least in part via the computing device 102 of FIG. 12. Thus, the network interface 118 of the computing device 102 may enables the server 152 and/or particle monitoring system 154 to communicate with/receive data from the particle processing systems 156 and 158 through the communication network 160. The communication network 160 may include Internet, intranet, LAN (Local Area Network), WAN (Wide Area Network), MAN (Metropolitan Area Network), wireless network (for example, using IEEE 802.11 or Bluetooth), or other network configurations. In addition the network may use middleware, such as CORBA (Common Object Request Broker Architecture) or DCOM (Distributed Component Object Model) to allow a computing device on the network 160 to communicate directly with another computing device that is connected to the network 160.

In the network environment 160, the server 152 and/or particle monitoring system 154 may provide the particle processing systems 156 and 158 with software components or products under a particular condition, such as a license agreement. The software components or products may include one or more components of the application 120 of FIG. 12. For example, the server 152 or particle monitoring system 154 may analyze and compare adjusted output representative of a particle characteristic for the plurality of particle processing systems 156 and 158 across the network environment 150.

Although the teachings herein have been described with reference to exemplary embodiments and implementations thereof, the disclosed systems, methods and non-transitory storage medium are not limited to such exemplary embodiments/implementations. Rather, as will be readily apparent to persons skilled in the art from the description taught herein, the disclosed systems, methods and non-transitory storage medium are susceptible to modifications, alterations and enhancements without departing from the spirit or scope hereof. Accordingly, all such modifications, alterations and enhancements within the scope hereof are encompassed herein.

What is claimed:

1. A computer-implemented method for controlling a particle processing system having a particle inspection system to reduce variability using processed flow cytometry data, the method comprising:
   receiving, by a processor, a baseline value for a population's first characteristic for a first population of particles, the baseline value generated from an analysis of a first set of data associated with the first population of particles flowing through a first flow path during a first particle processing operation, wherein the first population of particles is associated with a first particle type;
   processing, using the processor, a second set of data associated with a second population of particles flowing through a second flow path different than the first flow path during a second particle processing operation to generate a plurality of individual particle values for the first characteristic, the second population of particles being of the same particle type as the first particle type;
   generating, using the processor, adjustment factors based on the population's baseline value for the first characteristic of the first population of particles and the individual particle values for the first characteristic associated with the second population of particles;
   applying, using the processor, the adjustment factors to detected output values representative of a second particle characteristic associated with the second population of particles during the second particle processing operation, the second particle characteristic being different from the first characteristic, to generate an adjusted second set of particle data; and
   controlling one or more operational parameters of the particle inspection system relative to the second flow path based on the adjusted second set of particle data.

2. The method of claim 1, wherein the first set of data is associated with a first particle processing system and the second set of data is associated with a second particle processing system different than the first particle processing system.

3. The method of claim 2, wherein the second particle processing system is located at a geographic location different from a geographic location of the first particle processing system.

4. The method of claim 1, wherein the first set of data is associated with a first particle inspection system and the second set of data is associated with a second particle inspection system different than the first particle inspection system.

5. The method of claim 1, further comprising:
   collectively analyzing the first set of data and the adjusted second set of particle data to develop common sorting criteria for a particle sorting operation.

6. A particle analyzing system comprising:
   at least one processor configured to perform the method according to claim 1.

7. The method of claim 1, wherein the population's first characteristic is an average or a common velocity of the first population of particles flowing through the first flow path, and wherein the individual particle's first characteristic is a particle velocity.

8. The method of claim 1, wherein the second particle characteristic is a particle pulse area.

9. The method of claim 1, wherein the second particle characteristic is a particle pulse height.

10. The method of claim 1, wherein the second particle characteristic is a particle fluorescence.

11. The method of claim 1, wherein the second particle characteristic is a particle light extinction.

12. The method of claim 1, further comprising:
determining values of the second particle characteristic for the first set of particles flowing through the first flow path;
visually displaying the values of the second particle characteristic for the first set of particles; and
visually superimposing the adjusted particle data for the second particle characteristic associated with the second set of particles flowing through the second flow path onto the visually displayed values of the second particle characteristic for the first set of particles flowing through the first flow path.

13. A method for controlling a particle processing system having a particle inspection system to reduce variability using adjusted flow cytometry data, the method comprising:
determining, during a particle processing operation, an average or a common velocity of a first set of particles flowing through a first flow path, wherein the first set of particles are associated with a first particle type;
determining, during the same particle processing operation, particle velocities for a second set of particles flowing through a second flow path different than the first flow path, wherein the second set of particles are the same particle type as the first particle type;
generating, during the same particle processing operation, adjustment factors based on the average or the common velocity of the first set of particles and the particle velocities of the second set of particles;
applying, during the same particle processing operation, the adjustment factors to measurement values for a particle characteristic associated with the second set of particles, the particle characteristic being other than velocity, to generate adjusted particle data; and
controlling one or more operational parameters of the particle inspection system relative to the second flow path based on the adjusted particle data.

14. The method of claim 13, further comprising:
determining measurement values of the particle characteristic of the first set of particles flowing through the first flow path;
visually displaying the measurement values of the first set of particles; and
visually superimposing the adjusted particle data from the second set of particles flowing through the second flow path onto the visually displayed measurement values from the first set of particles flowing through the first flow path.

15. The method of claim 13, wherein the first and second flow paths are provided on a single microfluidic chip.

* * * * *